US011615866B2

(12) United States Patent
Smith et al.

(10) Patent No.: US 11,615,866 B2
(45) Date of Patent: Mar. 28, 2023

(54) SYSTEMS AND METHODS FOR AUTOMATED MONITORING AND REPLENISHMENT OF GENETIC MATERIAL RESERVES

(71) Applicant: SAPPHIROS LABORATORIES LLC, Boston, MA (US)

(72) Inventors: Robin Y. Smith, Boston, MA (US); Sunil Anant Gupta, Boston, MA (US)

(73) Assignee: SAPPHIROS LABORATORIES LLC, Boston, MA (US)

( * ) Notice: Subject to any disclaimer, the term of this patent is extended or adjusted under 35 U.S.C. 154(b) by 735 days.

(21) Appl. No.: 16/482,945

(22) PCT Filed: Feb. 1, 2018

(86) PCT No.: PCT/US2018/016377
§ 371 (c)(1),
(2) Date: Aug. 1, 2019

(87) PCT Pub. No.: WO2018/144691
PCT Pub. Date: Aug. 9, 2018

(65) Prior Publication Data
US 2019/0355441 A1    Nov. 21, 2019

Related U.S. Application Data

(60) Provisional application No. 62/584,603, filed on Nov. 10, 2017, provisional application No. 62/453,481, filed on Feb. 1, 2017.

(51) Int. Cl.
*G16B 50/30* (2019.01)
*G01N 1/02* (2006.01)

(52) U.S. Cl.
CPC .............. *G16B 50/30* (2019.02); *G01N 1/02* (2013.01); *G01N 2001/028* (2013.01)

(58) Field of Classification Search
CPC .......... G16B 50/30; G16B 50/00; G01N 1/02; G01N 2001/028
See application file for complete search history.

(56) References Cited

U.S. PATENT DOCUMENTS

2011/0017733 A1* 1/2011 Polettini ................. C12Q 1/56
220/200
2014/0304012 A1* 10/2014 Marom .................. G06Q 40/08
705/4

(Continued)

FOREIGN PATENT DOCUMENTS

EP        3315594 B1 *  2/2020 .............. C12M 1/34

OTHER PUBLICATIONS

International Preliminary Report on Patentability for International Application No. PCT/US2018/016377 dated Aug. 6, 2019.

(Continued)

*Primary Examiner* — Francis C Gray
(74) *Attorney, Agent, or Firm* — Foley Hoag LLP; Erik A. Huestis; Sameer K. Pai

(57) ABSTRACT

A meter value that reflects the amount of genetic material stored in a reserve is stored in a database for each reserve in a bank. Meter values allow a user to track the amount of genetic material in the reserves of a bank without needing to physically measure or disturb the reserves unnecessarily. As users withdraw and deposit genetic material from and into a reserve, the meter value is changed to reflect the change in the amount of genetic material in the reserve. In certain embodiments, the use of meter values enables accurate and instant accounting of a large number of reserves of genetic material for a large number of individuals. Users and/or individuals may be notified when a meter value falls below a threshold. Notifications may prompt a user to generate (Continued)

additional genetic material from biological sample or an individual to provide additional biological sample.

20 Claims, 11 Drawing Sheets

(56) References Cited

U.S. PATENT DOCUMENTS

| | | | |
|---|---|---|---|
| 2015/0193581 A1* | 7/2015 | Kaminski | G16B 50/30 |
| | | | 705/3 |
| 2018/0173842 A1* | 6/2018 | Smith | G16B 20/40 |
| 2018/0246089 A1* | 8/2018 | Chou | G16B 50/00 |
| 2019/0362531 A1* | 11/2019 | Smith | G16B 20/20 |

OTHER PUBLICATIONS

International Search Report and Written Opinion for International Application No. PCT/US2018/016377 dated Apr. 26, 2018.

* cited by examiner

| Gene | Result | |
|---|---|---|
| ALDH2 — Alcohol Tolerance | (Adapt) | (Adapt) (Normal) |
| CYP1A2 — Caffeine Metabolism | (Adapt) | (Normal) (Gifted) |
| MCM6 — Lactose Intolerance | (Adapt) | (Normal) (Gifted) |
| OR10A2 — Cilantro Aversion | (Adapt) | (Normal) (Gifted) |
| TAS2R38 — Bitter Taste (Part 1) | (Adapt) | (Normal) (Gifted) |
| TAS2R38 — Bitter Taste (Part 2) | (Adapt) | (Normal) (Gifted) |
| TAS2R38 | (Adapt) | (Normal) (Gifted) |

Food Sensitivity

FIG. 3D

YOUR PERSONAL FUEL

The FUEL assessment decodes information in your unique DNA, giving you unprecedented insights into the way your body processes different foods and nutrients. Once you understand your nutrition-related DNA, you can tailor your eating habits to support a new diet, avoid adverse food reactions, and maximize the impact of vitamins.

FIG. 3C

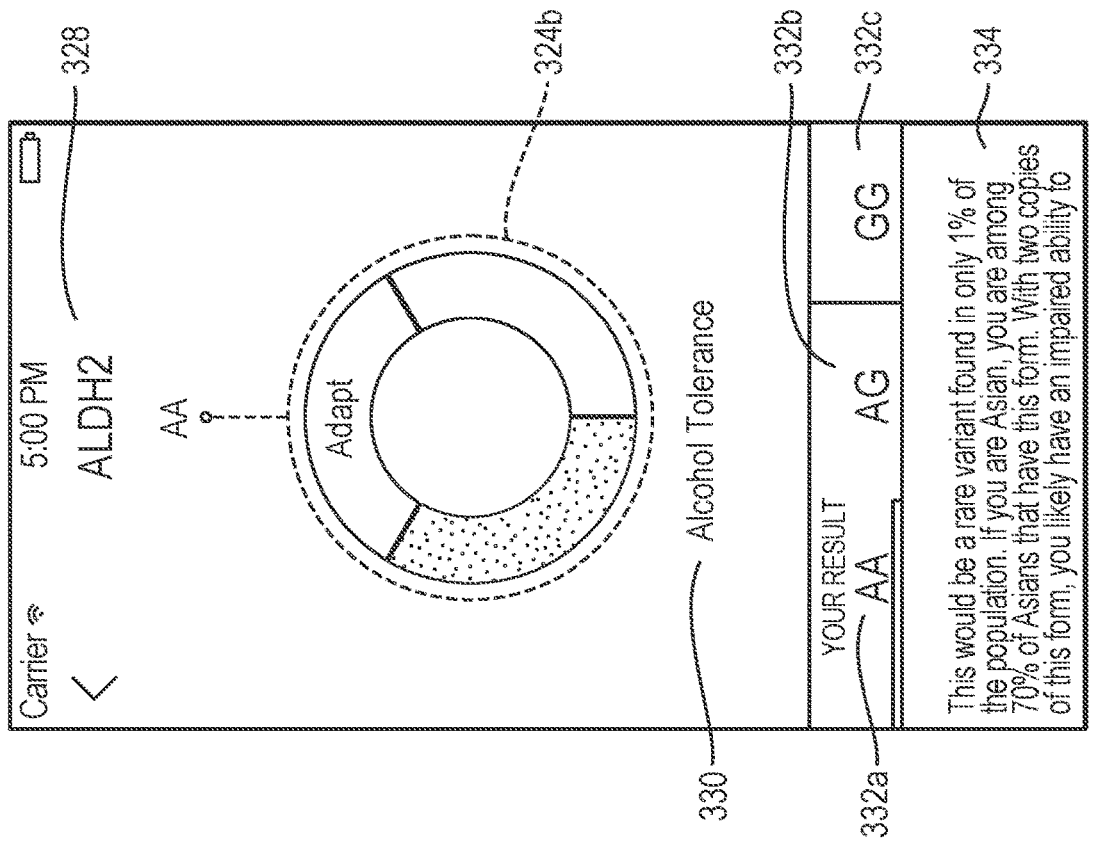

# EXPORTED BY: GUEST
# EXPORTED DATE: 10/10/2016 06:58:39 GMT-04:00
# STUDY NAME: 2016-10-10-G20072XMED
# EXPERIMENT TYPE: ENDPOINT
# INSTRUMENT TYPE: StepOne AND StepOnePlus SYSTEMS
# SOFTWARE VERSION NUMBER: 1.3
# CREATION DATE: 10/04/2016 07:36:37 GMT-04:00
# CREATED BY: GUEST
# LAST MODIFIED DATE: 10/10/2016 06:58:05 GMT-04:00
# LAST MODIFIED BY: GUEST
# TEMPLATE FILE NAME: N/A
# TEMPLATE ORIGINATING STUDY NAME: N/A
# TEMPLATE CREATION DATE: N/A
# TEMPLATE CREATED BY USER ID: N/A
# TEMPLATE SOFTWARE VERSION NUMBER: N/A

| SAMPLE ID | PLATE BARCODE | GENE SYMBOL | NCBI SNP REFERENCE | ASSAY NAME OR ID | ALLELE 1 | ALLELE 2 |
|---|---|---|---|---|---|---|
| RONEN147 | | CYP1A2 | rs762551 | C_8881221_40 | A | A |
| RONEN147 | | DRD4,DEAF1,SCT | rs1800955 | C_7470700_30 | T | T |
| RONEN147 | | FOXP2 | rs6980093 | C_11437347_10 | G | G |
| RONEN147 | | MTHFR,CLCN6 | rs1801133 | C_1202883_20 | G | G |
| RONEN147 | | NQO1,NFAT5 | rs1800566 | C_2091255_30 | G | G |
| RONEN147 | | ACTRT3,TERC,MYNN | rs12696304 | C_407063_10 | C | G |

FIG. 5

SYSTEMS AND METHODS FOR AUTOMATED MONITORING AND REPLENISHMENT OF GENETIC MATERIAL RESERVES

CROSS REFERENCE TO RELATED APPLICATIONS

This application claims the benefit of U.S. Provisional Application No. 62/453,481, filed Feb. 1, 2017 and U.S. Provisional Application No. 62/584,603, filed Nov. 10, 2017, the contents of each of which are hereby incorporated by reference herein in their entirety.

FIELD OF THE INVENTION

This invention relates generally to systems and methods for facilitating monitoring and replenishment of stored genetic material.

BACKGROUND OF THE INVENTION

Genomes hold much valuable information that can be used to better understand biological characteristics and traits of humans and animals. Much research is being conducted to establish relationships between the human genome and biological characteristics and traits, in particular. Single nucleotide polymorphisms (SNPs) are specific sites identified in particular genes that influence biological characteristics and traits different depending on the particular polymorphism of an individual. Different polymorphisms of the nucleotides at a specific site influence the relevant characteristic or trait differently. The influence of an individual's polymorphism on his/her trait can be positive or negative. Many relationships between the variants of SNPs and their corresponding biological characteristics and traits have been established and many more possible relationships are currently undiscovered and under investigation.

Until recently, characterizing a genome was prohibitively expensive such that very few individual genomes had been fully or partially characterized. Techniques utilized in genotyping a genome required significant resources that limited genotyping to laboratory use in scientific research and related areas. Developments of cost-effective equipment and procedures for genotyping have made personal genotyping feasible. The output of genetic information from such genotyping procedures still requires expertise in the biological sciences to understand.

In order for individuals to gain an understanding of their genome, they may provide biological samples to an organization for genotyping. The individual can obtain their biological sample in any number of ways and send it to the organization. One or more assays are run to at least partially genotype the individual based on genetic material extracted from the biological sample. Typical genetic testing depletes the biological sample provided by an individual. In certain research or commercial settings, biological sample and/or genetic material is retained in order to allow for future genetic experiments or tests (e.g., genotyping) to be performed in the future. Each experiment or test uses some amount of genetic material, which slowly depletes the amount stored. Complete depletion of stored genetic material prevents further genetic testing from being performed, requiring an individual to provide an additional biological sample or additional genetic material to be derived from remaining stored biological sample.

Individuals may also have biological sample material stored in cell repositories for purposes of supporting regenerative medicine. For example, induced pluripotent stem cells (iPS cells) may be produced from a blood sample (or other biological substance sample), then stored in a repository for ongoing and/or future use.

There is a need for systems and methods that facilitate storage of genetic material used for genomic research and genetic testing and tracking of the amount of genetic material stored. By allowing a user (operator) to obtain an assessment of the amount of genetic material remaining in a store, the user can appropriately plan and conduct experiments and/or tests without interruption to their workflow or delay in providing desired genetic (e.g., genomic) information to individuals.

SUMMARY

Reserves of genetic material are stored in a bank for use in genetic experiments and/or testing. A meter value that reflects the amount of genetic material stored in a reserve is stored in a database for each reserve in the bank. Meter values allow a user (operator) to track the amount of genetic material in the reserves of a bank without needing to physically measure or disturb the reserves unnecessarily, which may otherwise result in a negative change in the state of the genetic material. As users withdraw and deposit genetic material from and into a reserve, the meter value is changed to reflect the change in the amount of genetic material in the reserve. In certain embodiments, the use of meter values enables accurate and instant accounting of a large number of reserves of genetic material for a large number of individuals. Users and/or individuals may be notified when a meter value falls below a threshold. Notifications may prompt a user to generate additional genetic material from biological sample or an individual to provide additional biological sample.

In one aspect, the invention is directed to a method of monitoring (e.g., automatically) amounts of genetic material (e.g. DNA, e.g. RNA) stored in a reserve of genetic material extracted from biological samples of individuals (e.g. saliva, e.g. blood, e.g. tissue, e.g. cheek cells (e.g. collected via a cheek (buccal) swab, e.g. urine, e.g. hair, e.g. induced pluripotent stem cells generated from adult cells of individuals), the method comprising: for each of a plurality of individuals whose genetic material is contained in a bank, storing, by a processor of a computing device, a meter value that reflects an amount (e.g. grams, e.g., ng, e.g. mols, e.g., nmols, e.g. microliters (i.e. when genetic material is the solute in a solution of fixed concentration)) of the genetic material stored in a reserve of each individual's genetic material (e.g. the meter value is an estimated amount of genetic material stored in the reserve; e.g. the meter value is an estimated lower bound corresponding to an estimated minimum amount of genetic material stored in the reserve); and for each of one or more withdrawals or deposits of genetic material from/into the bank, updating, by the processor, the meter value of corresponding reserve(s) of genetic material to reflect an amount (e.g. grams, e.g., ng, e.g. mols, e.g., nmols) of genetic material remaining in the corresponding reserve(s).

In certain embodiments the method further comprises: determining, by the processor, for each of a plurality of reserves in the bank, whether the meter value is below a minimum threshold of an amount of genetic material to be maintained in the reserve of an individual; and responsive to determining that the meter value is below a minimum threshold value for a given reserve, triggering, by the processor, a notification (e.g., a graphical rendering in a software application) (e.g., that collection of additional genetic material from the individual associated with the reserve is needed) (e.g., that displays the meter value of each reserve for which the meter value is below the minimum threshold). In certain embodiments, the triggering of the notification comprises issuing an alert [e.g. an email, e.g. a text message, e.g. an in-app notification, e.g. a push notification sent to a computing device (e.g. a smartphone, e.g. a tablet computer) of the individual associated with the reserve] of low reserve amount (e.g. wherein the alert comprises an identification of the reserve and/or the individual associated with the reserve, e.g. wherein the alert comprises the meter value).

In certain embodiments, triggering of the notification comprises automatically issuing, by the processor, a request to supply the individual associated with the reserve with a kit for providing a replenishment biological sample (e.g. to an inventory management system, e.g., to an order fulfillment center).

In certain embodiments, the kit comprises instruments for collection of the replenishment biological sample from the individual associated with the reserve [e.g., wherein the kit comprises one or more instruments selected from the group consisting of: (A) an instrument for collecting cheek cells (e.g., one or more cheek (buccal) swabs); (B) an instrument for collecting a saliva sample (e.g., a saliva collection tube); (C) an instrument for collecting a blood sample (e.g., a syringe and blood collection tube; e.g., a portable phlebotomy kit; e.g., a home finger prick kit); (D) an instrument for collecting a urine sample (e.g., a urine specimen cup); and (E) an instrument for collecting a hair sample].

In certain embodiments, the kit comprises one or more cheek (buccal) swabs.

In certain embodiments, the kit comprises a prepaid, preaddressed mailing envelope for sending the replenishment biological sample to a facility for processing (e.g., extraction of genetic material; e.g., derivation of iPSCs therefrom) and/or storage.

In certain embodiments, the kit comprises a label comprising an anonymous identifier [e.g., an alphanumeric code; e.g., a graphical code (e.g., a barcode; e.g., a Quick Response (QR) code)] that identifies the reserve of genetic material associated with the individual [e.g., but comprises no other identifying information about the individual (e.g., such that the anonymous identifier label obscures the individual's identity)].

In certain embodiments, the method comprises providing (e.g., mailing) the kit to the individual.

In certain embodiments, the method further comprises, responsive to determining that the meter value is below a minimum threshold value for a given reserve, replenishing the given reserve with additional genetic material extracted from a biological sample from the individual associated with the reserve (e.g., a stored biological sample from the individual associated with the reserve; e.g., a replenishment biological sample provided by the individual associated with the reserve). In certain embodiments, the additional genetic material is extracted from induced pluripotent stem cells generated from adult cells [e.g. fibroblasts (e.g. obtained via a skin biopsy), e.g. keratinocytes (e.g. obtained from a hair sample), e.g. blood cells, e.g. renal epithelial cells (e.g. obtained from a urine sample)] from the individual associated with the reserve.

In certain embodiments, the method comprises, initially (e.g. prior to performing any measurements using the genetic material stored in the reserve): for each of a plurality of individuals, receiving (e.g., determining), by the processor, an initial value reflecting an amount of genetic material initially present in the reserve of genetic material associated with the individual (e.g. the initial value is an estimated amount of genetic material initially present in the reserve; e.g. the initial value is an estimated lower bound corresponding to an estimated minimum amount of genetic material initially present in the reserve); and storing, by the processor, the received initial value as the meter value. In certain embodiments, the initial value is based on an amount of genetic material extracted from a corresponding biological sample from the individual associated with the reserve and deposited in the reserve (e.g. an estimated amount of genetic material extracted from the corresponding biological sample; e.g. an estimated lower bound corresponding to an estimated minimum amount of genetic material extracted from the corresponding biological sample).

In certain embodiments, the method comprises, for each of the one or more withdrawals (e.g., withdrawals for purposes of conducting a genetic test): receiving (e.g. determining), by the processor, a usage value that reflects the amount (e.g. grams, e.g. mols) of genetic material removed in the withdrawal; and updating, by the processor, the meter value for the corresponding reserve using the usage value.

In another aspect, the invention is directed to a system for monitoring (e.g., automatically) amounts of genetic material (e.g. DNA, e.g. RNA) stored in a reserve of genetic material extracted from biological samples of individuals (e.g. saliva, e.g. blood, e.g. tissue, e.g. cheek cells (e.g. collected via a cheek (buccal) swab, e.g. urine, e.g. hair, e.g. induced pluripotent stem cells generated from adult cells of individuals), the system comprising: a processor; and a non-transitory computer readable memory having instructions stored thereon, wherein the instructions, when executed by the processor, cause the processor to: for each of a plurality of individuals whose genetic material is contained in a bank, store, by the processor, a meter value that reflects an amount (e.g. grams, e.g., ng, e.g. mols, e.g., nmols, e.g. microliters (i.e. when genetic material is the solute in a solution of fixed concentration)) of the genetic material stored in a reserve of each individual's genetic material (e.g. the meter value is an estimated amount of genetic material stored in the reserve; e.g. the meter value is an estimated lower bound corresponding to an estimated minimum amount of genetic material stored in the reserve); and for each of one or more withdrawals or deposits of genetic material from/into the bank, update, by the processor, the meter value of corresponding reserve(s) of genetic material to reflect an amount (e.g. grams, e.g., ng, e.g. mols, e.g., nmols) of genetic material remaining in the corresponding reserve(s).

In certain embodiments, the instructions, when executed by the processor, cause the processor to: determine, by the processor, for each of a plurality of reserves in the bank, whether the meter value is below a minimum threshold of an amount of genetic material to be maintained in the reserve of an individual; and responsive to determining that the meter value is below a minimum threshold value for a given reserve, trigger, by the processor, a notification (e.g., a graphical rendering in a software application) (e.g., that collection of additional genetic material from the individual associated with the reserve is needed) (e.g., that displays the meter value of each reserve for which the meter value is below the minimum threshold). In certain embodiments, the instructions, when executed by the processor, cause the processor to: when triggering the notification, issue an alert [e.g. an email, e.g. a text message, e.g. an in-app notification, e.g. a push notification sent to a computing device (e.g. a smartphone, e.g. a tablet computer) of the individual associated with the reserve] of low reserve amount (e.g. wherein the alert comprises an identification of the reserve and/or the individual associated with the reserve, e.g. wherein the alert comprises the meter value).

In certain embodiments, the instructions, when executed by the processor, cause the processor to: when triggering the notification, automatically issue, by the processor, a request to supply the individual associated with the reserve with a kit for providing a replenishment biological sample (e.g. to an inventory management system, e.g., to an order fulfillment center).

In certain embodiments, the kit comprises instruments for collection of the replenishment biological sample from the individual associated with the reserve [e.g., wherein the kit comprises one or more instruments selected from the group consisting of: (A) an instrument for collecting cheek cells (e.g., one or more cheek (buccal) swabs); (B) an instrument for collecting a saliva sample (e.g., a saliva collection tube); (C) an instrument for collecting a blood sample (e.g., a syringe and blood collection tube; e.g., a portable phlebotomy kit; e.g., a home finger prick kit); (D) an instrument for collecting a urine sample (e.g., a urine specimen cup); and (E) an instrument for collecting a hair sample].

In certain embodiments, the kit comprises one or more cheek (buccal) swabs.

In certain embodiments, the kit comprises a prepaid, preaddressed mailing envelope for sending the replenishment biological sample to a facility for processing (e.g., extraction of genetic material; e.g., derivation of iPSCs therefrom) and/or storage.

In certain embodiments, the kit comprises a label comprising an anonymous identifier [e.g., an alphanumeric code; e.g., a graphical code (e.g., a barcode; e.g., a Quick Response (QR) code)] that identifies the reserve of genetic material associated with individual [e.g., but comprises no other identifying information about the individual (e.g., such that the anonymous identifier label obscures the individual's identity)].

In certain embodiments, the instructions, when executed by the processor, cause the processor to, initially (e.g. prior to performing any measurements using the genetic material stored in the reserve): for each of a plurality of individuals, receive (e.g., determining), by the processor, an initial value reflecting an amount of genetic material initially present in the reserve of genetic material associated with the individual (e.g. the initial value is an estimated amount of genetic material initially present in the reserve; e.g. the initial value is an estimated lower bound corresponding to an estimated minimum amount of genetic material initially present in the reserve); and store, by the processor, the received initial value as the meter value. In certain embodiments, the initial value is based on an amount of genetic material extracted from a corresponding biological sample from the individual associated with the reserve and deposited in the reserve (e.g. an estimated amount of genetic material extracted from the corresponding biological sample; e.g. an estimated lower bound corresponding to an estimated minimum amount of genetic material extracted from the corresponding biological sample).

In certain embodiments, the instructions, when executed by the processor, cause the processor to, for each of the one or more withdrawals (e.g., withdrawals for purposes of conducting a genetic test): receive (e.g. determining), by the processor, a usage value that reflects the amount (e.g. grams, e.g. mols) of genetic material removed in the withdrawal; and update, by the processor, the meter value for the corresponding reserve using the usage value.

BRIEF DESCRIPTION OF THE FIGURES

The foregoing and other objects, aspects, features, and advantages of the present disclosure will become more apparent and better understood by referring to the following description taken in conjunction with the accompanying drawings, in which:

FIG. 3C is a screenshot of the GUI showing a summary of the product that appears when the information ("i") button of FIG. 3B is selected, according to an illustrative embodiment;

FIG. 3D is a screenshot of the GUI of FIG. 3A showing the interface that appears when a particular category of the selected product is selected, according to an illustrative embodiment;

FIG. 3E is a screenshot of the GUI of FIG. 3A showing the interface that appears when a particular SNP object of the selected category is selected, according to an illustrative embodiment;

FIG. 3F is a screenshot of the GUI showing further additional information that can be viewed by scrolling when the particular SNP object is selected, according to an illustrative embodiment;

FIG. 5 is portion of a text file comprising genotyping data, according to an illustrative embodiment;

Definitions

Figure 1:
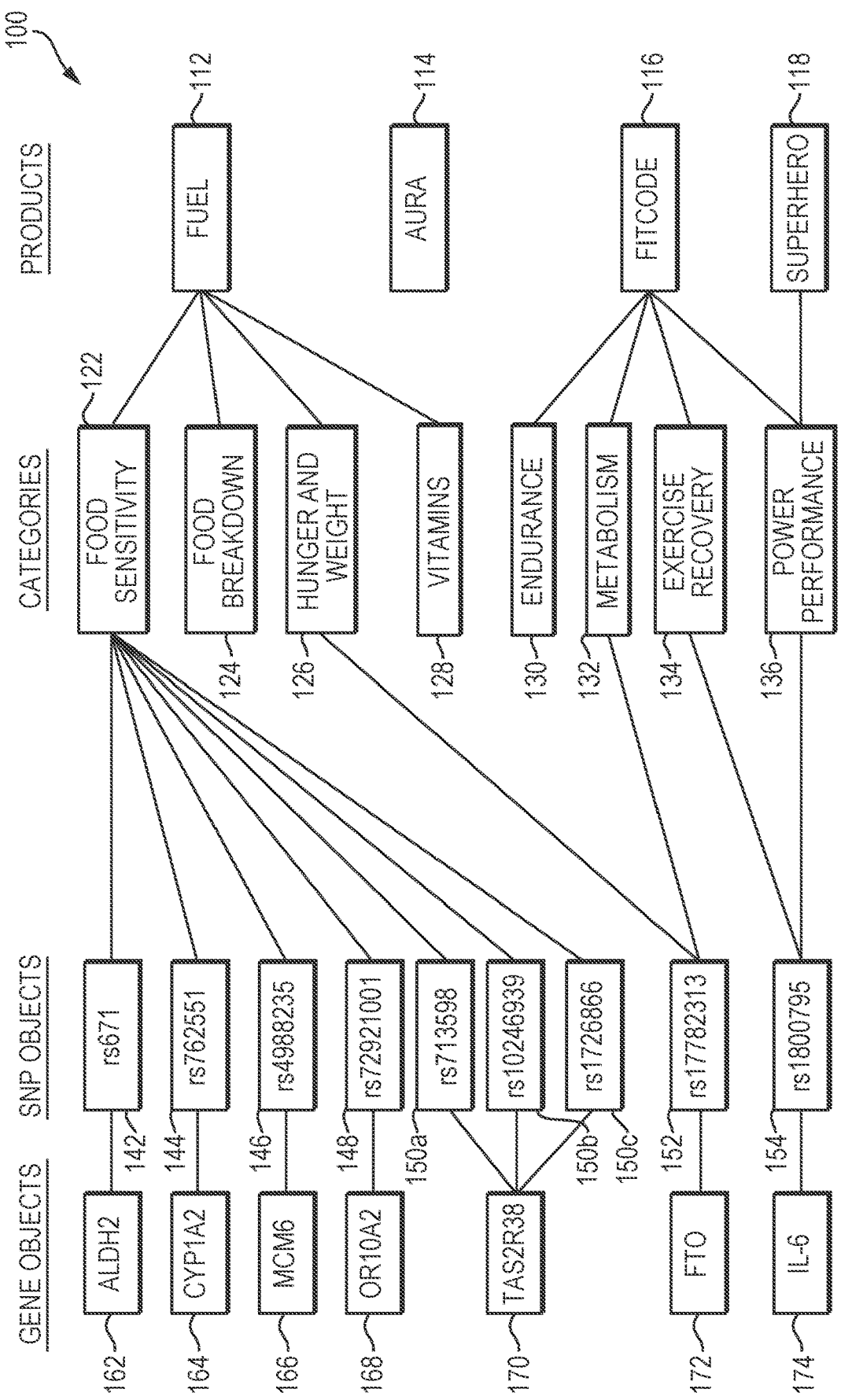
FIG. 1 is a block diagram illustrating associations between different data structures provided in accordance with the systems and methods described herein, according to an illustrative embodiment.

In order for the present disclosure to be more readily understood, certain terms used herein are defined below. Additional definitions for the following terms and other terms may be set forth throughout the specification.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Organization: As used herein, the term "organization" refers to an entity that performs genetic tests or otherwise uses or consumes stored biological samples and/or genetic material. The entity may be a company, individual, research group, research laboratory, non-profit organization, laboratory, hospital, medical organization, or medical testing facility. In certain embodiments, an organization performs genetic tests for research purposes. In certain embodiments, an organization performs genetic tests as a service or part of a service requested or purchased by an individual. In certain embodiments, the genetic tests an organization performs are genotyping tests.

Bank: As used herein, the term "bank" refers to a system, apparatus, or location where genetic material and/or biological sample is stored. Genetic material may be derived (e.g., extracted) from a biological sample provided by an individual to the organization that owns and/or operates the bank. In certain embodiments, biological samples are stored in a bank separate from a bank that stores genetic material extracted therefrom.

Individual: As used herein, the term "individual" refers to someone who provides a biological sample to an organization for use in genetic testing and/or experimentation. In certain embodiments, an individual uses an assessment graphical user interface in order to view information about a genome. The individual may supply one or more biological samples to be genotyped in order for a personal genetic profile assessment to be formed. The individual may purchase or be given access to one or more products in order to view a personal genetic profile assessment.

User: As used herein, the term "user" refers to someone associated with an organization who conducts and/or assists in conducting genetic testing and/or experimentation. In certain embodiments, a user is employed by an organization.

Reserve: As used herein, the term "reserve" refers to an amount of genetic material stored in a bank.

Meter value: As used herein, the term "meter value" refers to a value that reflects the amount of genetic material in a reserve stored in a bank. A meter value may be a percentage of a maximum capacity for a reserve, a value empirically measured or estimated from the amount of genetic material in a reserve, or a value that indicates fullness of the capacity of a reserve (e.g., a number on a scale from 1-5 or 1-10).

Variant: As used herein, the terms "variant" refers to a specific variation of a specific SNP occurring in the genetic material of a population. In certain embodiments, a variant is a specific combination of a first allele of a first copy of an individual's genetic material (e.g. corresponding to an individual's paternal DNA) and a second allele of a second copy of an individual's genetic material (e.g. corresponding to an individual's maternal DNA), as occurs in diploid organisms (e.g. humans).

Qualifier: As used herein, the term "qualifier" refers to a classification (e.g. a label) of a particular variant of a given SNP. The qualifier associated with a given variant is the particular classification (e.g. label) of that variant. For example, a given variant may be associated with a particular qualifier of a predefined set of possible qualifiers. For example, a given variant may be associated with a qualifier selected from a group of labels such as "Adapt," "Normal," and "Gifted." In certain embodiments, for a given variant of a given SNP, a qualifier corresponds to a classification of the given variant based on (i) the prevalence of the given variant within a population (e.g. if the variant is common, e.g. if the variant is rare) and/or (ii) a health-related phenotype associated with the variant. For example, a common variant may be associated with the qualifier "Normal". A rare variant that confers a disadvantageous phenotype, such as a predisposition to high cholesterol, may be associated with the qualifier "Adapt" (e.g. classified as rare and disadvantageous). A rare variant that confers an advantageous phenotype, such as a predisposition to lower cholesterol, may be associated with the qualifier "Gifted" (e.g. accordingly, the variant is classified as rare and advantageous).

Variant object: As used herein, the term "variant object" refers to a data structure corresponding to (e.g. that is used to represent) a specific variant of a physical SNP and/or gene within a given genome (e.g., the genome of a human).

SNP object: As used herein, the term "SNP object" refers to a data structure corresponding to (e.g. that is used to represent) a specific single nucleotide polymorphism (SNP). In certain embodiments, a SNP object comprises a SNP reference that identifies the specific SNP to which the SNP object corresponds. The SNP reference may be an alphanumeric code such as an accepted name of the SNP or other identifying mark or label capable of being stored electronically. The SNP reference may be an alphanumeric code such as a National Center for Biotechnology Information (NCBI) database reference number.

Gene object: As used herein, the term "gene object" refers to a data structure corresponding to (e.g. that is used to represent) a specific physical gene within a given genome (e.g. the human genome).

Genotyping data: As used herein, the term "genotyping data" refers to data obtained from measurements of a genotype. Measurements of a genotype performed on a biological sample identify the particular nucleotide(s) (also referred to as "bases") that is/are incorporated at one or more particular positions in genetic material extracted from the biological sample. Accordingly, genotyping measurements for a particular individual are measurements performed on a biological sample of from the individual, and which identify the particular nucleotides present at one or more specific positions within their genome.

Genotyping data may be measurements of particular genes (e.g., portions of an individual's genetic sequence, e.g., DNA sequence), or SNPs. For example, a genotyping measurement of a particular SNP for an individual identifies the particular variant of that SNP that the individual has. A genotyping measurement of a particular gene for an individual identifies the particular nucleotides that are present at one or more locations within and/or in proximity to the gene for the individual. For example, genotyping measurements of a particular gene may identify the particular variants of one or more SNPs associated with a particular gene.

In certain embodiments, genotyping data is obtained from a multi-gene panel. In certain embodiments, genotyping data is obtained from assays (e.g., TaqMan™ assays) that detect one or more specific variants of specific SNPs. In certain embodiments, genotyping data is obtained from genetic sequencing measurements. In certain embodiments, genotyping data is generated in response to a purchase or request by an individual. In certain embodiments, genotyping data comprises data for a portion of a genotype (e.g., of an individual). In certain embodiments, genotyping data comprises all available measurements of a genotype (e.g., of an individual).

Category: As used herein, the term "category" refers to a data structure corresponding to (e.g. that is used to represent) a particular health-related trait or characteristic.

Product, Genetic Profile Product, Personal Genetic Profile Product: As used herein, the terms "product," "genetic profile product," and "personal genetic profile product," refer to a data structure corresponding to (e.g. that is used to represent) a general class of health-related traits and/or characteristics. In certain embodiments a product is associated with one or more categories that correspond to health-related traits and characteristics related to the general class of health-related traits and characteristics to which the product corresponds.

Graphical Control Element: As used herein, the term "graphical control element" refers to an element of a graphical user interface element that may be used to provide user and/or individual input. A graphical control element may be a textbox, dropdown list, radio button, data field, checkbox, button (e.g., selectable icon), list box, or slider.

Associate, Associated with: As used herein, the terms "associate," and "associated with," as in a first data structure is associated with a second data structure, refer to a computer representation of an association between two data structures or data elements that is stored electronically (e.g. in computer memory).

Provide: As used herein, the term "provide", as in "providing data", refers to a process for passing data in between different software applications, modules, systems, and/or databases. In certain embodiments, providing data comprises the execution of instructions by a process to transfer data in between software applications, or in between different modules of the same software application. In certain embodiments a software application may provide data to another application in the form of a file. In certain embodiments an application may provide data to another application on the same processor. In certain embodiments standard protocols may be used to provide data to applications on different resources. In certain embodiments a module in a software application may provide data to another module by passing arguments to that module.

DESCRIPTION OF THE INVENTION

Presented herein are systems and methods related for automatically monitoring amounts of genetic material contained in a bank that comprises genetic material of a plurality of individuals.

Meter Values and Storage of Biological Samples and Genetic Material

An individual provides a biological sample to an organization for use in characterizing genetic characteristics of genetic material contained in the biological sample. The individual takes one or more biological samples to provide to the bank. Biological samples may be, for example, saliva, blood, tissue, cheek cells, urine, hair, or induced pluripotent stem cells (iPSCs) generated from adult cells. Such biological samples may be taken by any commonly known method such as, for example, a cheek swab. Biological samples may be biological samples of the individual or they may belong to a person or animal related to the individual. In some embodiments, biological samples are from a non-human animal. For example, an individual may supply a biological sample of their pet in order to understand genomic information about the pet to assist in providing better care. The animal may be a pet or may be an animal cared for by an individual. For example, the individual may be a veterinarian or a caretaker at a zoo charged with caring for the animal. In some embodiments, an individual provides a biological sample of a ward to whom the individual is a guardian. For example, a parent may supply a biological sample to understand genomic information about his/her child in order to improve his/her childrearing.

Individuals may also have biological sample material stored in cell repositories for purposes of supporting regenerative medicine. For example, induced pluripotent stem cells (iPS cells) may be produced from a blood sample (or other biological substance sample), then stored in a repository for ongoing and/or future use.

Biological samples contain genetic material (e.g., DNA, RNA) that can be characterized by the organization. During processing and for any length of time after, genetic material derived from biological samples may be stored in a bank. In certain embodiments, an individual provides a biological sample to a company in order for the company to extract DNA from the biological sample for use in genotyping. In certain embodiments, the extracted DNA is stored in a bank when not in use.

An organization may store the genetic material of a large number of individuals for a prolonged period of time. A large bank of genetic material requires an accurate record of the amount of genetic material stored for reference in planning, conducting, and logging genetic tests, assays, or other related experiments. The accurate record may be a database or array stored electronically on a computer for reference using a computer (e.g., over a web interface or on a locally run piece of software).

A database or array will store a meter value that reflects the amount of genetic material in a bank for each individual for which genetic material has been extracted (i.e., from a biological sample). In this way, a user can view a database (e.g., visualized on a display) that indicates the meter value for each individual with genetic material in the bank in order to monitor the amount of genetic material of one or more individuals possessed by the organization.

A meter value is a value that reflects the reserve of an individual's genetic material as stored. The meter value may be stored as a value in any conventional unit that reflects the amount available in the bank. For example, the meter value may be a value in grams, nanograms, moles, nanomoles, liters, milliliters, microliters, or similar. In certain embodiments, a meter value is stored in nanograms. In certain embodiments, a meter value is stored in microliters. When a meter value is stored in a volumetric unit, a standard concentration of the genetic material in a solvent may be used by an organization such that the meter value is proportional to the amount of genetic material stored in the bank. In certain embodiments, the meter value is an estimate of the amount of genetic material (i.e., the meter value is an average, median, or similar statistical estimator of the amount stored in the bank as derived from the usage history of the reserve of the individual's genetic material). The meter value may be an estimated lower bound corresponding to an estimated minimum amount of genetic material stored in the reserve.

A meter value is updated when the amount of genetic material in a bank changes. The amount of genetic material in a bank may change due to a withdrawal or deposit from the bank. For example, genetic material is withdrawn from a bank when a user runs an experiment or test (e.g., an assay) on the genetic material. In certain embodiments, the meter value of a reserve is lowered by a set amount for each withdrawal for a test due to each test requires a fixed amount of genetic material. In certain embodiments, a user runs a PCR-based SNP genotyping assay (e.g., a TaqMan™ SNP genotyping assay).

Genotyping Assays and Storage and Presentation of Genetic Profile Assessments

In certain embodiments, a genotyping assay is performed by a user as prompted by an individual's request for additional genomic information. For example, as described herein, genotyping assays that result in withdrawals of genetic material from the bank may occur when the individual purchases or is given access to additional products in a personal genetic profile assessment. As described herein, personal genetic profile products represent genotyping assays that measure sets of related (e.g., in terms of the various health related phenotypes that they influence) SNPs. As individuals purchase various genotyping assays represented by products in order to, e.g., find out different types of information about their unique genetic makeup, genetic material from their reserves in the bank in order to perform the purchased genotyping assays.

In certain embodiments, performing such genotyping assays, creating individual personal genetic profile assessments, and presenting information to an individual is facilitated by a flexible and hierarchical data structure framework. Approaches for performing genotyping assays and creating personal genetic profile assessments using flexible data structure frameworks and organization of genotyping assays based on products are also described in PCT Application No. PCT/US17/67264, filed Dec. 19, 2017, and PCT Application No. PCT/US17/67272, filed Dec. 19, 2017, the contents of each of which are hereby incorporated by reference herein in their entirety.

A. Flexible Data Structure Framework

Turning to FIG. 1, in certain embodiments, in order to provide an individual not only with their personal genetic profile assessment, but also convey information related to the particular traits and characteristics that are influenced by the specific SNP variants present in their genetic material in an organized and intuitive fashion, the systems and methods described herein provide a framework comprising an intuitive hierarchical organization of data structures. The framework provides for storing relationships (e.g. associations) between particular SNPs, health-related traits and characteristics, and general classes of such health-related traits and characteristics, based on the specific phenotypes that each particular SNP influences.

In certain embodiments, a first class of data structures, referred to herein as products, are used to represent different general classes of health-related traits and characteristics. In certain embodiments, a product data structure corresponds to a particular assessment ordered (e.g., purchased by the individual), in which unique versions of genes and/or SNPs that an individual has that influence the particular general class of health-related traits and characteristics that the corresponding product represents are identified (e.g., via genotyping measurements). In certain embodiments, each product has a name (e.g. a product data structure comprises a name (e.g. text data representing the name)) that provides a convenient, and memorable way to refer to the product. For example, a particular product 112 (e.g. named "FUEL™") is used to represent a class of traits corresponding to the way in which an individual's body processes different foods and nutrients. Another product 114 (e.g. named "AURA™") is used to represent a class of traits corresponding to skin health. Another product 116 (e.g. named "FITCODE™") is used to represent a class of traits corresponding to physical fitness. Another product 118 (e.g. named "SUPERHERO™") is used to represent a class of traits corresponding to physical and intellectual performance. In certain embodiments, a name of a product is the same as the name under which a particular assessment is offered for sale. For example, assessments FUEL™, FITCODE™, AURA™ and SUPERHERO™ are offered for sale by Orgi3n, Inc. of Boston Mass.

In certain embodiments, each product is in turn associated with one or more of a second class of data structures, referred to as categories. In certain embodiments, each category corresponds to a particular health-related trait or characteristic (e.g. food sensitivity, food breakdown, hunger and weight, vitamins, skin uv sensitivity, endurance, metabolism, joint health, muscle strength, intelligence). In certain embodiments, the categories with which a particular product is associated each correspond to different health-related traits or characteristics that are related to the general class of health-related traits or characteristics to which the particular product corresponds (e.g. the general class of health-related traits or characteristics that the product represents). As with products, in certain embodiments, each category has a name (e.g. a category data structure comprises a name (e.g. text data representing the name)) that provides a convenient, and memorable way to refer to the category.

In turn, each category is associated with one or more SNP objects, each SNP object corresponding to a specific SNP. Each SNP object associated with a particular category corresponds to a specific SNP that influences a specific health related phenotype that relates to the trait or characteristic to which the particular category corresponds. Each SNP object may identify the specific SNP to which it corresponds via a SNP reference that the SNP object comprises. The SNP reference may be an alphanumeric code such as an accepted name of the SNP or other identifying mark or label capable of being stored electronically. The SNP reference may be an alphanumeric code such as a National Center for Biotechnology Information (NCBI) database reference number.

For example, the schematic of FIG. 1 shows an example of series of products, categories, and SNP objects that are associated with each other. Associated gene objects, to be described in the following, are also shown. The different products and categories are identified by their particular names, and the SNP objects each are identified by a respective SNP reference each comprises. In the example of FIG. 1, the SNP references are NCBI database reference numbers.

Figure 2:
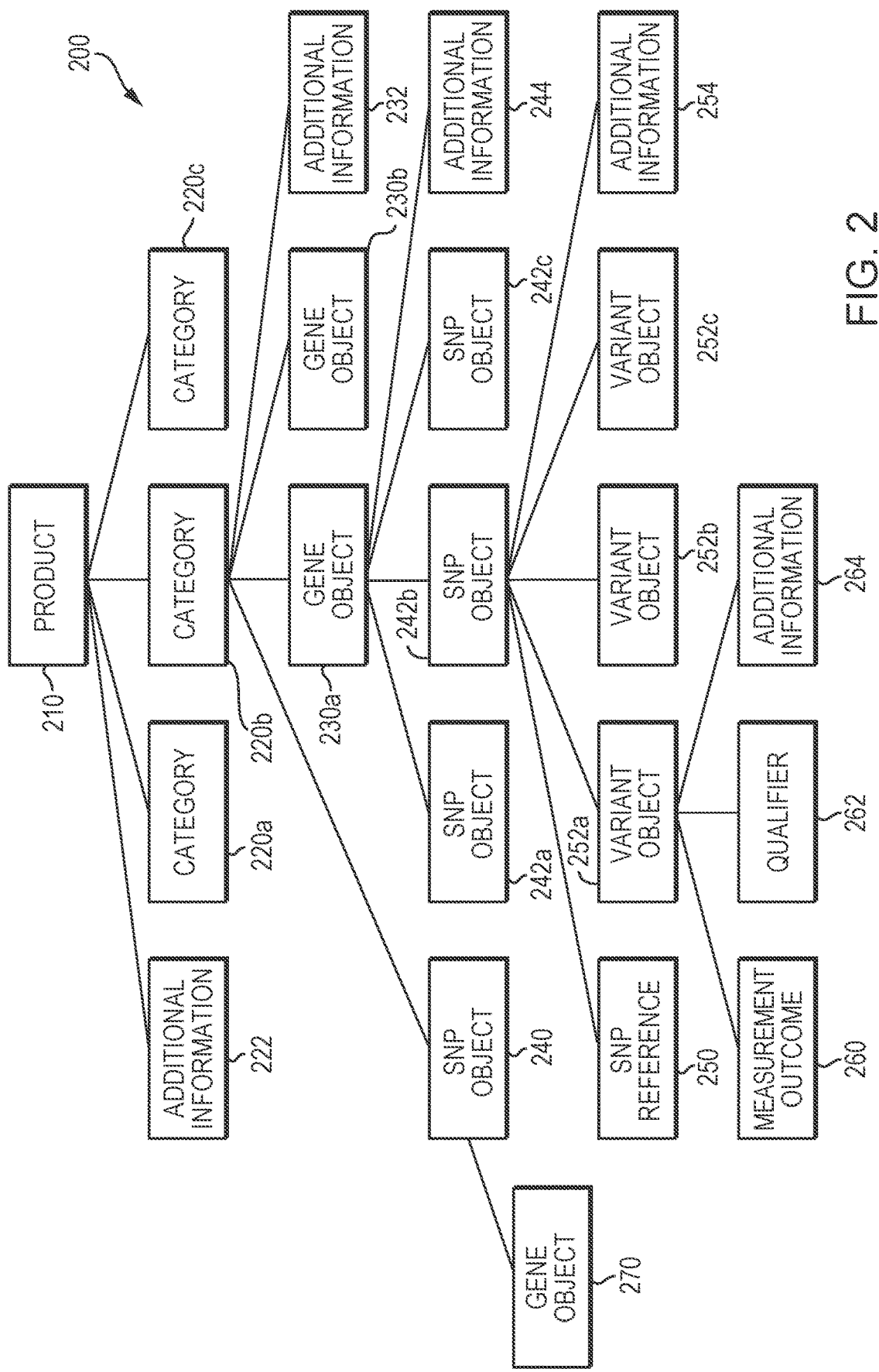
FIG. 2 is a block diagram showing an organizational hierarchy of a personal genetic profile product, according to an illustrative embodiment.

The "FUEL™" product 112 is associated with categories such as "Food Sensitivity" 122, "Food Breakdown" 124, "Hunger and Weight" 126, and "Vitamins" 128. Several SNP objects corresponding to specific SNPs that influence phenotypes related to an individual's sensitivity to different types of foods, and, accordingly, are associated with the "Food Sensitivity" category 122 are shown. In FIG. 2, the lines connecting the SNP objects to different categories indicate the association of each particular SNP object with one or more different categories. The associations may be direct associations or indirect associations (e.g., through mutual association with an intermediate data structure not shown).

For example, SNP object 132 corresponds to the rs671 SNP, which influences the manner in which an individual processes alcohol. In particular, depending on the particular variant of the rs671 SNP that an individual has, the individual may process alcohol normally, or be impaired in their ability to process alcohol, and likely suffer from adverse effects resulting from alcohol consumption, such as flushing, headaches, fatigue, and sickness. Accordingly, providing an individual with knowledge of the particular variant of the rs671 SNP that they have may allow them to modify their behavior accordingly, for example, by being mindful of the amounts of alcohol that they consume (e.g. on a regular basis, e.g. in social settings).

Other SNP objects corresponding to SNPs that influence food sensitivity related phenotypes, and, accordingly, are associated with the "Food Sensitivity" category 222 are shown. For example, SNP object 144 corresponds to the rs762551 SNP that influences caffeine metabolism, SNP object 146 corresponds to the rs4988235 SNP that influences lactose intolerance, and SNP object 148 corresponds to the rs72921001 SNP that influences an aversion to the herb Cilantro (e.g. depending on the particular variant of this SNP that an individual has, they may either perceive Cilantro as pleasant tasting, or bitter and soap-like in taste).

In certain examples, multiple SNPs are associated with a particular phenotype and, accordingly, the SNP objects to which they correspond may be grouped together. For example, three SNPS—rs713598 (corresponding to SNP object 150*a*), rs10246939 (corresponding to SNP object 150*b*), and rs1726866 (corresponding to SNP object 150*c*), —influence the sensitivity of an individual to bitter tasting foods (e.g. cabbage, broccoli, cauliflower, kale, brussel sprouts, and collard greens), and, accordingly, their enjoyment of or aversion to such foods.

SNPs correspond to specific locations within or nearby (e.g. a SNP may occur in a promotor region that influences transcription of a particular gene, e.g. a SNP may occur within 5 kb upstream or downstream of a particular gene, e.g. a SNP may occur within 100 kb upstream or downstream of a particular gene, e.g. a SNP may occur within 500 kb upstream or downstream of a particular gene, e.g. a SNP may occur within 1 Mb upstream or downstream of a particular gene) genes in an individual's genetic material. Accordingly, in certain embodiments, as shown in FIG. 1, each SNP object is associated with a gene object that corresponds to the particular gene within or nearby to which the SNP to which the SNP object corresponds is present. For example, the rs671 SNP corresponds to a location within the ALDH2 gene; the rs762551 SNP corresponds to a location within the CYP1A2 gene, the rs4988235 SNP occurs within the MCM6 gene, and the rs72921001 SNP occurs within the OR10A2 gene. Accordingly, SNP object 142 (corresponding to the rs671 SNP) is associated with gene object 162 (corresponding to the ALDH2 gene). Similarly, SNP object 144 (corresponding to the rs762551 SNP) is associated with gene object 162 (corresponding to the CYP1A2 gene), SNP object 146 (corresponding to the rs4988235 SNP) is associated with gene object 166 (corresponding to the MCM6 gene) and SNP object 148 (corresponding to the rs72921001 SNP) is associated with gene object 168 (corresponding to the OR10A2 gene).

Other SNPs objects correspond to SNPs that are nearby particular genes of interest and thereby influence phenotypes associated with expression of the gene. For example, rs12696304 is a SNP that lies 1.5 kb downstream from the TERC gene, and influences biological aging associated with the TERC gene. Accordingly, in one example, a SNP object corresponding to the rs12696304 SNP is associated a gene object corresponding to the TERC gene.

In certain embodiments, multiple SNPs of interest occur within a single gene. For example, the three SNPs related to bitter taste—rs713598, rs10246939, and rs1726866—occur within the TAS2R38 gene. Accordingly, SNP objects 150*a*, 150*b*, and 150*c*, which correspond to the rs713598, rs10246939, and rs1726866 SNPs, respectively, are all associated with a gene object 170 corresponding to the TAS2R38 gene.

In certain embodiments, different products correspond to different general classes of health-related traits and characteristics. For example, products may be based on particular organs (e.g. product 114, named "AURA™", is related to skin health), or particular habits, activities, or bodily functions. For example, food related biological characteristics and traits may be covered by a single products or a plurality of products. A single product or a plurality of products may be based on learning and brain function characteristics and traits. A single product or a plurality of products may be based on physical fitness (e.g., cardiovascular strength, agility, flexibility, muscular strength).

For example, as shown in FIG. 1, another product 116 (e.g. named "FITCODE™"), relates to a general class of physical fitness related traits, and, accordingly, comprises categories associated with endurance 130 ("Endurance"), metabolism 132 ("Metabolism"), the ability of an individual to recover effectively following exercises 134 ("Exercise Recovery"), and cardiovascular fitness and skeletal muscle makeup 136 ("Power Performance").

In certain embodiments, a particular SNP object is associated with two or more categories. For example, the rs17782313 SNP, occurring in the FTO gene, influences an individual's appetite. Accordingly, as shown in FIG. 1, the SNP object 152 corresponding to the rs17782313 SNP is associated with both the "Hunger and Weight" category 126 of the "FUEL™" product, and the "Metabolism" category 132 of the "FITCODE™" product. SNP object 152 is also associated with gene object 172, reflecting the fact that the rs17782313 SNP occurs in the FTO gene. In certain embodiments, as with the rs17782313 SNP object, each of a first category and a second category with which a particular SNP object is associated are associated with a different product. In certain embodiments, a particular SNP object is associated with a first category and a second category, and both the first category and the second category are associated with the same product.

For example, the SNP object 154 corresponding to the rs1800795 SNP of the IL-6 gene (accordingly, SNP object 154 is associated with gene object 174, which corresponds to the IL-6 gene) is associated with the "Exercise Recovery" category 134 and the "Power Performance" category 136, both of which are associated with the "FITCODE™" product 116. In addition, in certain embodiments, a category is associated with two or more products. For example, the "Power Performance" category 136 is associated with the "FITCODE™" product 116, as well as the "SUPER-HERO™" product 118, which provides an assessment of a general class of traits related to physical and intellectual performance.

Thus, by providing a framework comprising a hierarchical organization of data structures corresponding to products, categories, SNP objects, and gene objects, the systems, methods, and architectures described herein provide an intuitive and flexible approach to storing, updating, and creating new associations between different classes of health-related traits and characteristics, and the underlying genetic variations corresponding to different specific SNPs that influence them.

In certain embodiments the hierarchical organization of product, category, SNP object gene object, and variant object data structures serves as a flexible template that facilitates both the rapid creation of individual personal genetic profile assessments from genotyping measurements taken from a plurality of individuals, and the presentation of an individual's personal genetic profile assessment. In particular, an individual may purchase assessments corresponding to different products, in order to gain insight into the manner in which their personal genome influences the different general classes of health-related traits and characteristics to which each different product corresponds. Accordingly, an individual's personal genetic profile assessment corresponding to one or more products comprises, for each specific SNP associated with each category that is associated with each of the one or more products, an identification of the particular variant of the specific SNP that the individual has. Typically, the identification is obtained via one or more genotyping measurements performed on a biological sample taken from the individual (e.g. a blood sample, e.g. a cheek swab sample, e.g. a saliva sample, e.g., a hair sample, e.g., hair follicle cells).

In certain embodiments, an individual may purchase a first assessment corresponding to a first product, and provide a biological sample for genotyping. The individual's biological sample may be stored (e.g. cryogenically frozen). After a period of time, the individual may choose to purchase additional assessments corresponding to other products, and the individual's previously stored biological sample may be taken from storage for additional genotyping measurements of the additional SNPs that are associated with the new products. Moreover, in certain embodiments, additional new products may be created over time, and new assessments corresponding to new products offered to and purchased by individuals. In certain embodiments, as new information related to the influence of new and/or existing SNPs on different specific health related phenotypes is elucidated, new SNP objects and gene objects may be created, and new associations between them and new or existing categories and/or products established. In certain embodiments, existing personal genetic profile assessments of individuals are automatically updated to reflect new information.

In certain embodiments, in order to facilitate the creation and presentation of individual personal genetic profile assessments (e.g. corresponding to one or more different products) based on the framework described above, the product, category, SNP object, and gene object data structures described herein store a variety of information. In certain embodiments, product, category, SNP object, and gene object data structures are created and associated as a hierarchy of data structures to be later associated with the genotyping data of an individual. FIG. 2 is a block diagram of a hierarchy of data structures 200 of an example genetic profile product. In certain embodiments, a developer creates and stores one or more generic hierarchies of data structures in accordance with FIG. 2 that define one or more products that may be purchased and/or accessed by an individual. The hierarchies of data structures are generic in that they contain no personal information for any one individual, but instead define the collection of genes, SNPs, and variants that have relevance to the biological characteristics and/or traits that are encompassed by a product.

An exemplary data structure of each type is shown to be associated with sub-data structures in order to simplify presentation of the figure. It is understood that data structures may be associated to any number of other data structures in the hierarchy if the association is consistent with the associations shown in FIG. 2. For example, category 220b is associated with gene objects 230a-b while category 220c may be associated with one or more gene objects and/or SNP objects, but any such associations are not shown. In some embodiments, data structures may be created without also forming associations between other structures of relevant types. For example, unassociated or partially associated data structures may be created for planning purposes such as during product or category development (e.g., category 220a has no associations yet because its scope has not been determined yet by the user). For example, unassociated or partially associated data structures may be created to allow genotyping data to be associated with relevant gene objects or SNP objects in order to retain the data in a ready to use format in the event that the gene objects and/or SNP objects are later associated with one or more categories.

Referring now to FIG. 2, product 210 comprises three categories 220a-c and additional information 222. Additional information 222 may be a name of the product, an icon associated with the product, and/or a description of the product. Category 220b comprises two gene objects 230a-b, one SNP object 240, and additional information 232. Additional information 232 may comprise a name of the category, a background image associated with the category, an icon associated with the category, a category order identifier, and/or a description of the category. SNP object 240 is associated with gene object 270. Gene object 230a is associated to three SNP objects 242a-c. Categories may be associated directly to SNP objects, such as category 220b is associated with SNP object 240, or they may be associated indirectly such as SNP objects 242a-c are associated to category 220b via gene object 230a. The ability to form associations indirectly allows all SNP objects associated with a particular gene object to be associated with a category by forming a single association in cases where all SNP objects of a particular gene are relevant to a particular category. The ability to form associations directly allows a particular SNP object to be associated with a category without also forming an association with all other SNP objects associated with the gene object associated with the particular SNP object in cases where only one or a subset of SNP objects of a particular gene object are relevant to a category.

Gene object 230a is also associated with additional information 244. Additional information 244 may comprise one or more data structures comprising information such as a unique gene identifier that corresponds gene object 230a to a specific physical gene and descriptive information about the corresponding gene. The gene identifier may be an alphanumeric code such as an accepted name of the gene or other identifying mark or label capable of being stored electronically. Additional information may be stored as a single data structure or a plurality of data structures.

SNP object 242*b* is associated with SNP reference 250, and additional information 254. SNP reference 250 is a unique identifier of the SNP that corresponds the SNP object to a specific physical SNP. The SNP reference may be an alphanumeric code such as an accepted name of the gene or other identifying mark or label capable of being stored electronically. The SNP reference may be an alphanumeric code such as a National Center for Biotechnology Information (NCBI) database reference number. Additional information 254 may comprise one or more data structures with other descriptive information about the corresponding SNP.

Variants of a particular SNP can be represented within a corresponding SNP object using various combinations of data elements such as a measurement outcomes, and qualifiers. For example, a particular variant of a SNP can be identified by a measurement outcome, which is an identifier, such as an alphanumeric code, that identifies the specific alleles corresponding to the particular variant. For example, a measurement outcome such as the string "CC" identifies a first variant of the rs762551 SNP in which an individual has a cytosine (C) at the rs762551 position in each copy of their genetic material. A measurement outcome such as the string "AC" identifies a second variant of the rs762551 SNP in which an individual has a C in one copy and an adenine (A) in the other at the rs762551 position. A measurement outcome such as the string "AA" identifies a second variant of the rs762551 SNP in which an individual has an A at the rs762551 position in each copy of their genetic material. A qualifier is an identifier, such as an alphanumeric code, that identifies a classification of a variant, wherein the classification may be based on the prevalence of the variant within a population, a health-related phenotype associated with the variant, and/or other relevant classification bases. Additional information may also be included within a SNP object to describe a particular variant.

In certain embodiments, measurement outcomes and qualifiers that identify and classify, respectively the same variant are associated with each other to form a variant object associated with the SNP object. For example, variant object 252*a* comprises measurement outcome 260, qualifier 262. Variant object 252*a* is also comprises additional information 264. Qualifiers may be words or short phrases that characterize the variant. For example, "adapt" may be used to characterize variants that are uncommon and/or disadvantageous; "normal" may be used to characterize variants that are common and/or neither advantageous nor disadvantage; and "gifted" may be used to characterize variants that are uncommon and/or advantageous. Additional information 264 comprises a description of the variant. For example, the additional information comprises a description of the specific health-related phenotype that an individual with the variant represented by variant object 252*a* exhibits or an explanation of the prevalence of the variant. A SNP object may be associated with a variant object to represent each variant of the particular SNP to which it corresponds. For example, SNP object is associated with three variant objects 252*a-c*.

B. Presentation of Individual Personal Genetic Profile Assessments

In certain embodiments, an individual views their genomic information using an assessment graphical user interface (assessment GUI) that is populated using one or more products (e.g., one or more hierarchies of data structures, such as the exemplary hierarchy of FIG. 2) and the individual's personal genetic profile assessment. In certain embodiments, the individual's personal genetic profile assessment is associated with the one or more products using a plurality of associations such that the assessment GUI is populated using the plurality of associations. In some embodiments, the one or more products are personalized by updating the hierarchies of data structures to comprise the data of the individual's personal genetic profile assessment such that the assessment GUI is populated using one or more products modified to be personalized to the individual. The assessment GUI allows individuals to interactively view their genomic information by navigating through the layers of data structures from the product level down to the level of information for individual SNPs. FIGS. 3A-3H are snapshots of an exemplary assessment graphical user interface that an individual would use to view their genomic information.

Figure 3B:
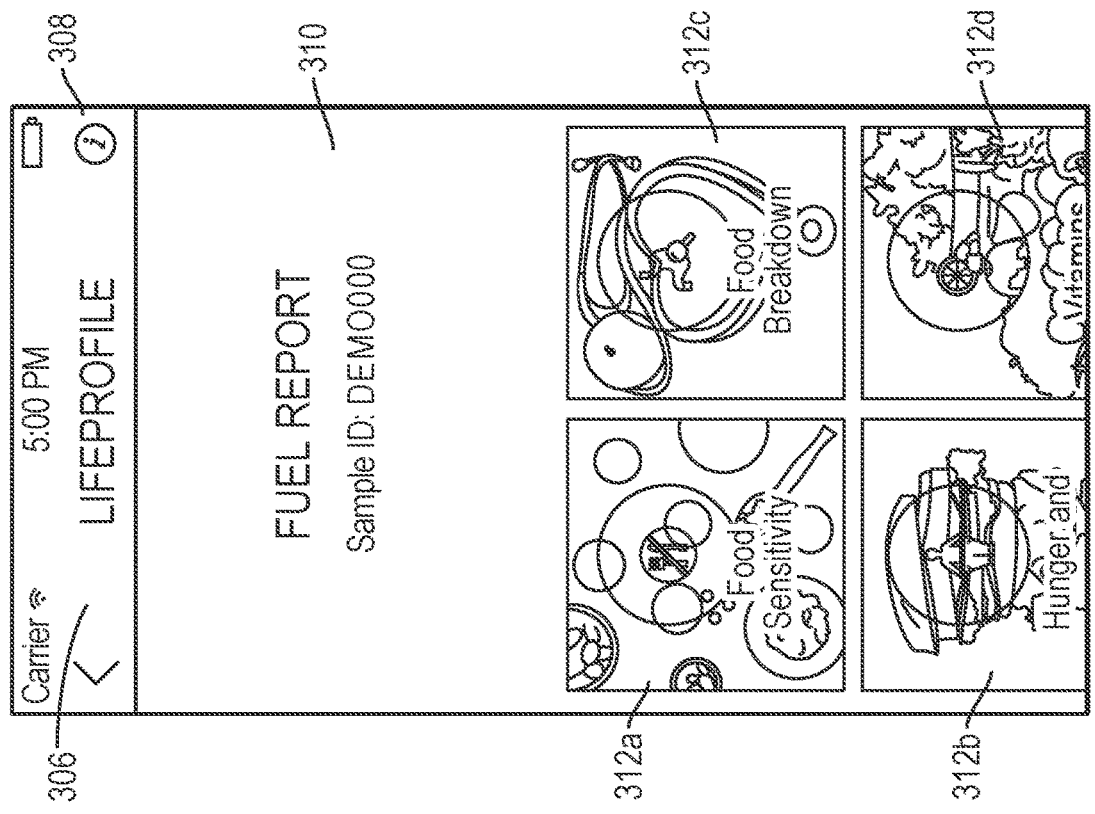
FIG. 3B is a screenshot of the GUI of FIG. 3A showing the interface that appears when a particular product is selected, according to an illustrative embodiment.
Figure 3A:
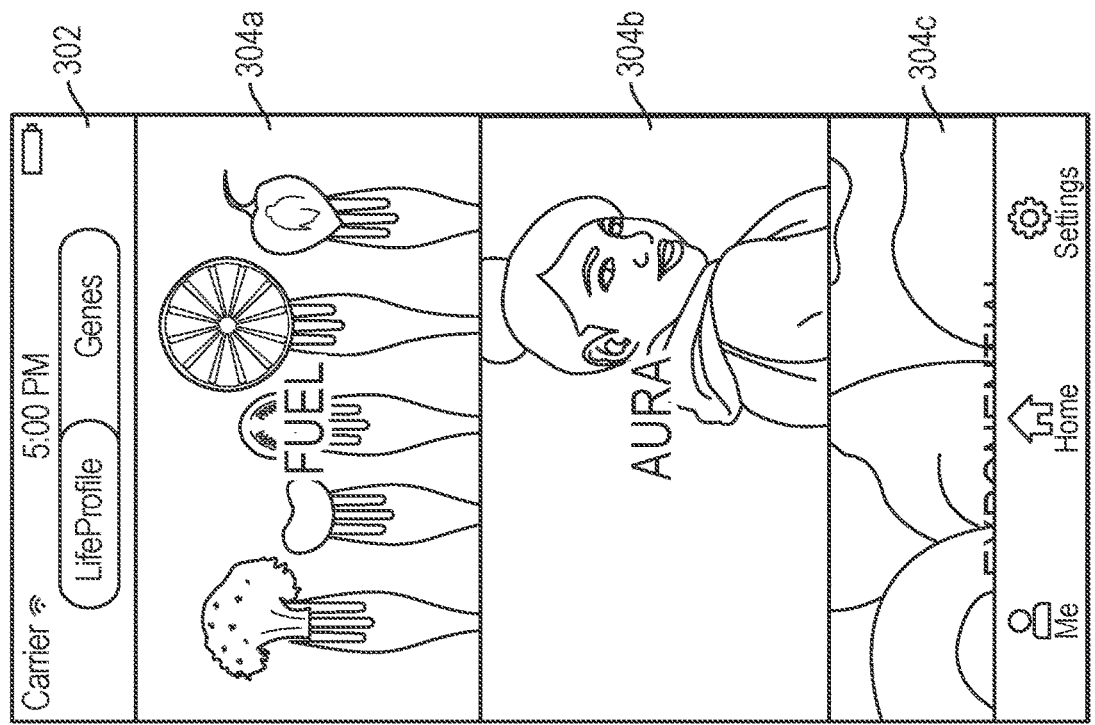
FIG. 3A is a screenshot showing a homescreen of a graphical user interface (GUI) that a user uses to view different products that summarize their genetic profile, according to an illustrative embodiment.

Referring now to FIG. 3A, the screenshot shows a home screen an individual uses to navigate to specific information about their personal genetic profile assessment. Three products 304*a-c* are visible: "FUEL™" 304*a*, "AURA™" 304*b*, "EXPONENTIAL™" 304*c*. Each product corresponds to a different set of genes that determine biological characteristics and traits. Selector 302 allows the individual to switch between his/her "LifeProfile™" that allows for navigation to specific information through the hierarchy of data structures, whereas Genes allows the individual to scroll through a listing of all SNPs corresponding to products that the individual has purchased or been given access to.

In certain embodiments, an assessment graphical user interface also includes a graphical control element for sharing data corresponding to an individual's personal genetic profile assessment (or a portion thereof) with one or more sharing entities. Sharing entities may be other individuals, people, or services with whom an individual wishes to share. For example, an individual may wish to share his or her entire personal genetic profile assessment with a friend, a spouse, or a social media service. Upon selection of the graphical control element for sharing, one or more graphical control elements may be provided for selecting which portions (e.g., products, categories, or a selected list of individual SNPs and/or genes) of a personal genetic profile assessment an individual would like to share (e.g., in the event that the individual would prefer certain portions of his or her personal genetic profile assessment remain private). In certain embodiments, the data is in a PDF report generated from the individual's personal genetic profile assessment.

Selecting a graphical control element for sharing may provide an individual with additional graphical control elements with which to select exactly with whom and by what method a personal genetic profile assessment (or portion thereof) is shared. For example, graphical control elements may be provided for selecting whether to text, email, or post the personal genetic profile assessment (or portion thereof) and other graphical control elements may be provided to allow an individual to select one or more recipients from among his contacts or enter contact information such as a phone number or email address. For example, an individual may select only certain friends or followers on a social media site with whom the personal genetic profile assessment (or portion thereof) is shared.

In certain embodiments, an individual uses a graphical control element for sharing in order to give access to other individuals using an assessment graphical user interface for viewing information about their genomes. For example, a first individual may use a graphical control element for sharing to give access to their personal genetic profile assessment to a spouse, wherein the spouse views the first individual's personal genetic profile assessment using an assessment GUI. In certain embodiments, an assessment GUI includes a graphical control element that an individual uses to select whose personal genetic profile assessment he or she is viewing. For example, the spouse may use such a graphical control element to toggle between viewing his or her own personal genetic profile assessment and the first individual's personal genetic profile assessment.

By selecting the "FUEL™" product from the LifeProfile™ listing of FIG. 3A, the individual sees the assessment GUI state of FIG. 3B. LifeProfile™ indicator 306 reminds the individual that he/she is using the LifeProfile™ navigation system. The information button 308 can be selected to view the brief description associated with the "FUEL™" product in its data hierarchy, as shown in FIG. 3C. Referring again to FIG. 3B, Fuel Report 310 provides space for a summary of the individual's "FUEL™" product genomic information. Categories 312a-d may be selected to view specific genomic information regarding different aspects of the individual's genome related to food and eating (e.g., different aspects of the "FUEL™" product). For each of the four categories, the individual sees the name of the category, the background image associated with the category, and the icon associated with the category. For example, category 312a is named Food Sensitivity, where the icon is a fork and knife with a slash, and the background image shows a variety of foods on a table.

Figure 3H:
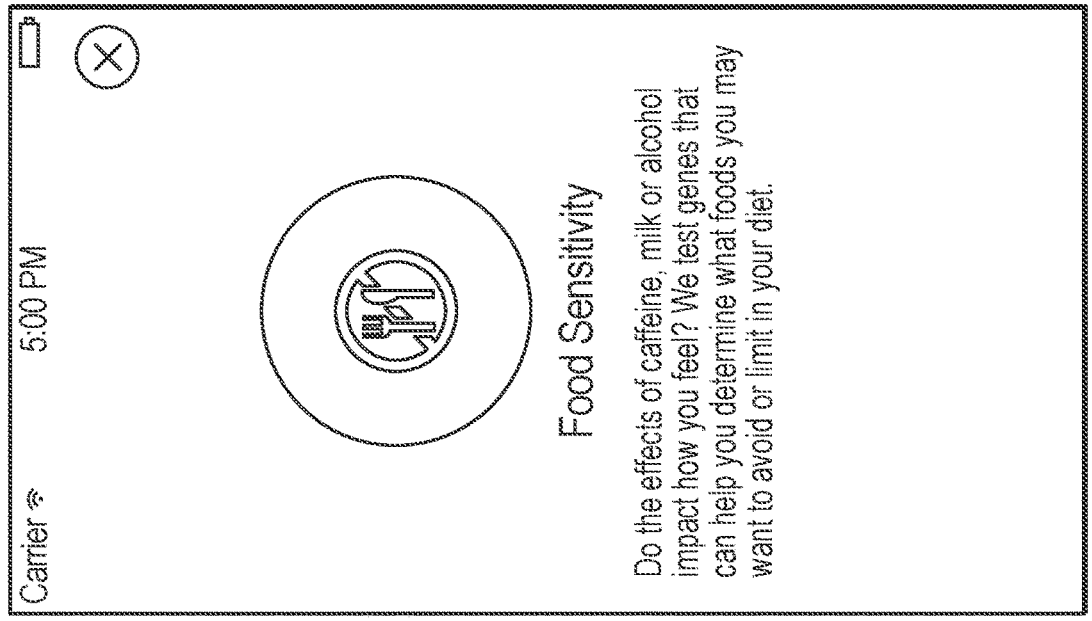
FIG. 3H is a screenshot of the GUI showing a summary of the category that appears when the information ("i") button of FIG. 3D is selected, according to an illustrative embodiment.

Selecting the Food Sensitivity category 312a brings the individual to a view of the assessment GUI shown in FIG. 3D. The information button 322 can be selected to view the brief description associated with the Food Sensitivity category, as shown in FIG. 3H. Referring again to FIG. 3D, the individual may scroll through a list of selectable control elements corresponding to each of the SNPs related to the category, wherein each selectable control element comprises brief summary information that the individual may use to determine which selectable control element to select. For example, the first selectable control element in the list shown in FIG. 3D comprises a short description of a SNP 316, a graphical representation of a gene identifier 314 corresponding to the SNP, and a graphical representation of the qualifier 324a associated with the variant corresponding to the individual's particular alleles of the SNP.

The short description of the SNP 316 characterizes the biological characteristic or trait influenced by the corresponding SNP in the individual's genome. For example, the short description of the SNP 316 is "Alcohol Tolerance." The individual would see that selecting the first selectable control element in the list would provide the individual with information about how the individual's genome influences his/her tolerance for alcohol consumption. The individual may select a particular selectable control element to view detailed information based on the short description of a SNP and/or the qualifier of the variant corresponding to his/her particular alleles of the SNP (as displayed by the graphical representation of the qualifier).

The graphical representation of the qualifier 324a is a graphic showing each of the qualifiers associated with the three variants corresponding to the SNP with the qualifier of the particular variant corresponding to the individual's alleles highlighted. Qualifiers may be words or short phrases that characterize the variant. For example, "adapt" may be used to characterize variants that are uncommon and/or disadvantageous; "normal" may be used to characterize variants that are common and/or neither advantageous nor disadvantage; and "gifted" may be used to characterize variants that are uncommon and/or advantageous. The graphical representation of the qualifier 324a highlights the qualifier associated with the variant corresponding to the individual's alleles in red. Different colors may be used to highlight different qualifiers in a graphical representation of a qualifier. For example, in FIG. 3D, when highlighted in a graphical representation of a qualifier, "adapt" qualifiers are highlighted in red, "normal" qualifiers are highlighted in blue, and "gifted" qualifiers are highlighted in green.

Some genes have multiple related SNPs. The related SNPs may influence a single biological characteristic or trait or a plurality of biological characteristics and/or traits. Each SNP may correspond to a unique selectable control element in the assessment GUI. For example, the graphical representation of the gene identifier 318 appears in two separate selectable control elements shown FIG. 3D since at least two unique SNPs relate to the gene corresponding to the graphical representation of the gene identifier 318. The two unique SNPs are differentiated by unique corresponding short descriptions 320a ("Bitter Taste (Part 1)") and 320b ("Bitter Taste (Part 2)"). Short descriptions 320a and 320b correspond to related SNPs that influence an individual's sensitivity to bitterness in food.

Selecting the first selectable control element identified by short description 316 ("Alcohol Tolerance") brings the individual to a view of the assessment GUI shown in FIG. 3H comprising detailed information regarding the SNP corresponding to the short description "Alcohol Tolerance." The graphical representation of the gene identifier 328 is shown at the top of the screen. A graphical representation of the qualifier 324b associated with the variant corresponding to the individual's particular alleles of the SNP identified in the first selectable control element. Graphical representation 324b displays both that the measurement outcome corresponding to the individual's alleles is "AA" and that the qualifier associated with this variant is "Adapt". The other two segments of the ring in graphical representation 324b relate to the other two variants corresponding to the SNP and are color coded to the associated qualifiers as described above. The graphical representation 324b is an alternative to the graphical representation 324a of FIG. 3D. Graphical control elements 332a-c indicate the measurement outcomes associated with each of the three variants corresponding to the SNP. Graphical control element 332a indicates that the individual's alleles correspond to the variant identified by the displayed measurement outcome (by displaying "Your Result" above the measurement outcome) as well as that information currently displayed below the row of graphical control elements 332a-c is associated with that variant (by displaying the light blue bar under the measurement outcome). A portion of description 334 associated with the variant identified in graphical representation 332a is visible. An individual may select other graphical control elements identified by other measurement outcomes to view information associated with other variants.

Figure 3G:
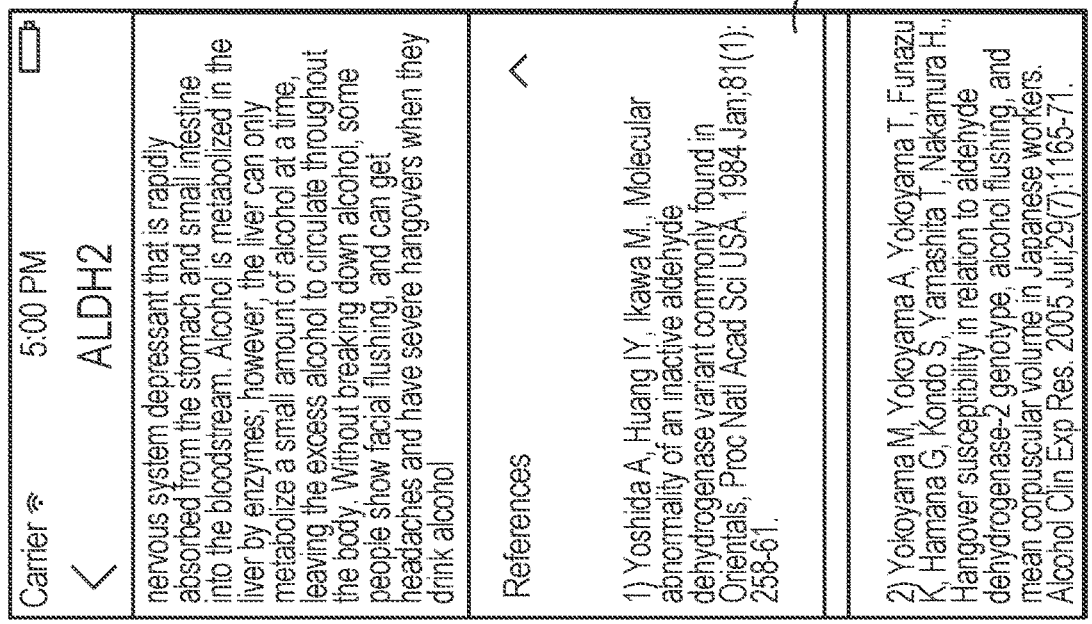
FIG. 3G is a screenshot of the GUI showing further additional information that can be viewed by scrolling further when the particular SNP object is selected, according to an illustrative embodiment.

Referring now to FIG. 3F, the individual may scroll in order to read more information regarding their genome. By scrolling, the complete description 334 may be read as may other additional information 336, which may be include a brief description associated with a SNP object corresponding to the SNP. Scrolling further, an individual can see references 338 that provide further detail related to the currently selected variant of the SNP object, as shown in FIG. 3G.

The assessment GUI shown in FIGS. 3A-3H is configured for display on mobile devices (e.g., smartphones, tablets, PDAs), but an assessment GUI may also be configured for viewing on a computing device using the web (e.g., with a laptop or desktop computer). The assessment GUI is populated using data associated with one or more products. A standardized graphical user interface element (e.g., widget) is used to create data and data structures as well as associations between existing and new data and data structures.

C. Automated Creation of Individual Personal Genetic Profile Assessments

Figure 4:
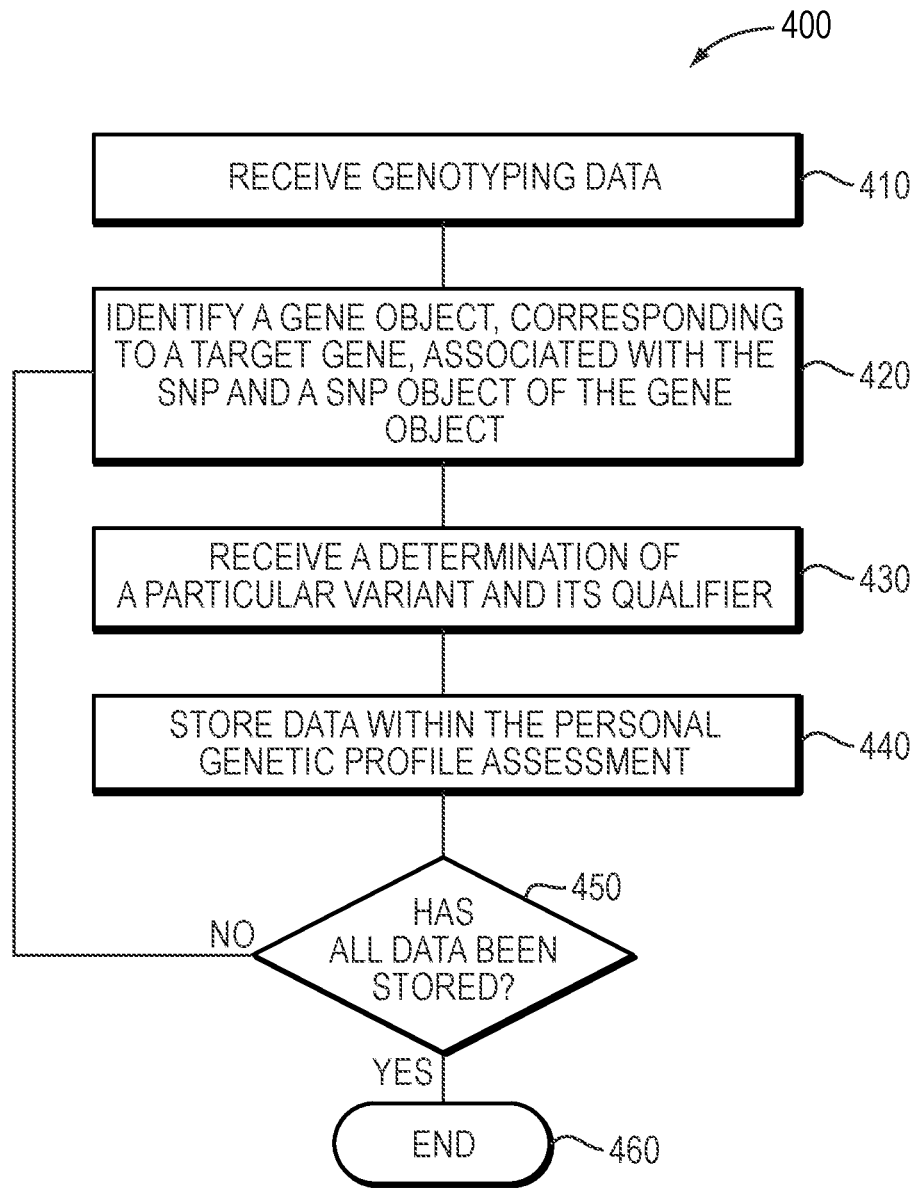
FIG. 4 is a block diagram showing a process for creating a personal genetic profile assessment, according to an illustrative embodiment.

In order to populate an assessment GUI to provide to an individual, genotyping data must be added to the individual's personal genetic profile assessment. FIG. 4 is a block diagram of a method 400 for adding genotyping data to an individual's personal genetic profile assessment. In step 410, a processor of a computing device receives genotyping data. In step 420, the processor identifies a gene object corresponding to a gene measured in the genotyping data and a SNP object corresponding to a SNP associated with the gene [e.g. the SNP occurring within the gene or occurring nearby the gene (e.g. within a promotor region that influences transcription of the gene, e.g. within 5 kb upstream or downstream of the gene, e.g. within 100 kb upstream or downstream of the gene, e.g. within 500 kb upstream or downstream of the gene, e.g. within 1 Mb upstream or downstream of the gene)]. In certain embodiments, genotyping data is stored as a table of data in a text file where each row corresponds to a unique SNP. In step 430, a particular variant of SNP represented by the identified SNP object and its associated qualifier are determined based on data from genotyping measurements. For example, data corresponding to the measurement outcome of a particular variant may be stored as one or more columns at the end of each row. In step 440, the data is stored in the individual's personal genetic profile assessment. In step 450, the processor determines if all data of the genotyping data has been stored. If all data has not been stored in the individual's personal genetic profile assessment, then the method returns to step 420. If all data has been stored, then the method ends 460. In some embodiments, the processor determines if unstored data exists by determining if there is a row of data in the genotyping data below the just processed row.

FIG. 5 shows exemplary genotyping data 500. Genotyping data may take the form of a text file saved by a user, wherein the text file is generated manually or as output from equipment for performing genotyping measurements (e.g. TaqMan™ SNP genotyping assays). FIG. 5 comprises 6 rows of genotyping data from a single biological sample ("RONEN147"). Each row corresponds to data for a different SNP. Each SNP of the genotyping data 500 is identified by at least a gene identifier 510 and a SNP reference 520. The gene identifier identifies the gene with which the SNP is associated. In certain embodiments, multiple (e.g. two or more) genes are associated with the SNP (e.g. the SNP may occur nearby two or more genes and influence phenotypes associated with each of the associated genes), and, accordingly, two or more corresponding gene identifiers are listed. Each SNP in the genotyping data has a corresponding variant identified by the allele measurements 530. The measurements "allele 1" and "allele 2" for a given SNP may be compared with measurement outcomes associated with the variants of a SNP object corresponding to the given SNP to populate an individual's personal genetic profile assessment.

The genotyping data in FIG. 5 used to populate an individual's personal genetic profile assessment is generated from one or more biological samples of the individual. However, the one or more biological samples used in populating an individual's personal genetic profile assessment may also be taken from a different human or a non-human animal. In some embodiments, genotyping data is generated from one or more biological samples of a non-human animal. For example, an individual may supply biological samples of their pet in order to understand genomic information about the pet to assist in providing better care. The animal may be a pet or may be an animal cared for by an individual. For example, the individual may be a veterinarian or a caretaker at a zoo charged with caring for the animal. In some embodiments, genotyping data is generated from one or more biological samples of a ward to whom the individual is a guardian. For example, a parent may supply one or more biological samples to genotyping data for their child in order to improve his/her childrearing.

Monitoring Meter Levels and Replenishment of Reserves

Genetic material is deposited into a bank, for example, when an individual provides an organization with one or more additional biological samples. As genetic material for each individual is stored as a separate reserve in a bank, the reserve of genetic material of an individual may be withdrawn from or deposited into as desired without impacting the reserves of other individuals also stored in the bank.

A user may check (e.g., proactively or automatically) the meter values for one or more (e.g., for each) reserves in a bank either individually or using certain criteria. For example, a user may enable a meter value check (i.e., meter value determination) that notifies the user to all reserves in a bank that have a meter value below a threshold. The threshold may be preset or may be selected by the user. The meter value check may run automatically or may be prompted by the user. An automatic notification may be the result of a meter value check that runs automatically with a certain frequency (e.g., daily, weekly, monthly). The notification alerts the user to which individuals with reserves stored in the bank have reserves whose meter value falls below the threshold. The meter value check may run, for example, each time that a withdrawal or deposit is made or it may be prompted by the purchase of a product of a personal genetic profile. The notification may provide identifying characteristics of the reserves and/or their meter value or it may prompt the user that collection of additional genetic material from individuals with low reserves is needed.

Notifications may alert a user visually (i.e., with a graphical display) or it may alert an individual directly. An individual may be alerted to the need to provide additional biological sample by an electronic means. For example, an individual may be alerted by email, text message, an in-app notification, a push notification, a phone call, or a voicemail. The individual may be notified of their current meter value or may be notified only qualitatively that their reserve is low.

In certain embodiments, one or more automatic actions are taken when an individual's reserve is determined to be below an established threshold. In certain embodiments, a kit for providing a replenishment biological sample is sent to an individual whose reserve has a meter value is determined to be below the established threshold. The kit may be sent based on a request sent automatically be an organization to a kit supplier at the instant of determination. For example, the kit may be sent from a fulfillment center. In certain embodiments, a letter may be sent to an individual informing them of the status of their reserve. In certain embodiments, an appointment may be scheduled to procure the replenishment biological sample from the individual when the reserve of the individual is determined to be low.

A variety of replenishment biological samples, such as saliva samples, blood samples, cheek cells, urine samples, hair samples, and the like, may be collected from an individual, conveniently in their home, using instruments provided in the kit sent to the individual.

For example, the kit may comprise an instrument for obtaining a saliva sample, such as a saliva collection tube into which the individual spits to provide their saliva sample.

For example, the kit may comprise an instrument for collecting a blood sample. Instruments for collecting a blood sample may include a home finger prick kit that an individual may use themselves to collect the blood sample via a finger prick. In certain embodiments, phlebotomy instruments may be provided to the individual e.g., in the form of a portable phlebotomy kit. The individual may be semi-automatically scheduled a visit from a phlebotomist or nurse for collection of the blood sample (e.g., the individual may be prompted, via an email, website, app, similar computerized approach, to select one or more available dates for the phlebotomist or nurse visit, and other aspects handled automatically by the system). The portable phlebotomy kit may be sent directly to the individual, or provided by the phlebotomist or nurse at the time of their visit.

In certain embodiments, cheek cells are collected, and the kit comprises one or more cheek (buccal) swabs that the individual may use to provide cheek cell samples.

In certain embodiments, the individual may provide a urine sample may be collected, for example using a urine specimen cup included in the kit.

In certain embodiments, the kit comprises instruments for collecting a hair sample (e.g., comprising one or more hairs), such as tweezers and/or collection tubes.

In certain embodiments, the kit comprises a prepaid, preaddressed mailing envelope for sending the replenishment biological sample to a facility for processing (e.g., extraction of genetic material; e.g., derivation of iPSCs) and/or storage. In certain embodiments, the kit comprises a label comprising an anonymous identifier that identifies the reserve of genetic material associated with the individual, but comprises no other identifying information about the individual. The anonymous identifier may be, for example, an alphanumeric code or a graphical code (e.g., a barcode; e.g., Quick Response (QR) code) that identifies the reserve of genetic material associated with the individual. The anonymous identifier label can be used to label the individual's biological sample. The individual may then mail their replenishment biological sample with their identity obscured. Without any other identifying information on the package or the replenishment biological sample provided by the individual, the individual's identity can thereby be obscured through the entire process from the time when they mail their biological sample through when genetic material is extracted and placed in their associated reserve.

In certain embodiments, a user has access to a first bank that stores biological samples and a second bank that stores genetic material. When the reserve of an individual is determined to have a meter value below a certain threshold, the user may be prompted to generate more genetic material from biological sample of the individual stored in the first bank. In some embodiments, the prompt comprises adding a task to a lab technician's task list to extract additional genetic material from biological sample of the individual soon. For example, biological sample may be stored as induced pluripotent stem cells (iPSCs) that can be used to generate additional genetic material when needed by a user. In this way, for example, the generation of excess genetic material can be avoided and costs to an organization associated with producing genetic material from biological sample can be deferred until necessary.

When a new reserve is added to a bank, an initial meter value is generated to be stored in the database for the bank. The initial meter value may be set by the user using software for interacting with the database. The initial meter value may be determined by a computing device, for example, based on an empirical measure received by the computing device (e.g., a mass or volume of genetic material and/or solution containing the genetic material). The empirical measure may be generated by a measuring apparatus connected (directly or indirectly) to the computing device. For example, a scale may be connected to a computer such that the mass of genetic material placed on the scale is received by the computer. A user may first indicate on the computer that a new reserve is being added to a bank (e.g., prior to placing the genetic material in or in the measuring apparatus connected to the computer). Such a method may additionally be used when a user is depositing or withdrawing genetic material from a reserve. For example, a user may need to indicate that a withdrawal is being made prior to making the withdrawal. In certain embodiments, a user manually inputs to a computing device amounts of genetic material being deposited (e.g., initially) or withdrawn from a bank.

An initial amount of genetic material may be estimated from the amount of biological sample used to generate the genetic material. For example, when using an established procedure for generating genetic material where the proportion of genetic material derived from starting biological sample can be calculated or estimated based on the parameters used in the procedure, the initial known amount of biological sample can be used to estimate the amount of genetic material that is to be stored in a bank. Such a calculation or estimation may additionally be used to update the meter value of a reserve when depositing genetic material into the reserve.

Figure 6:
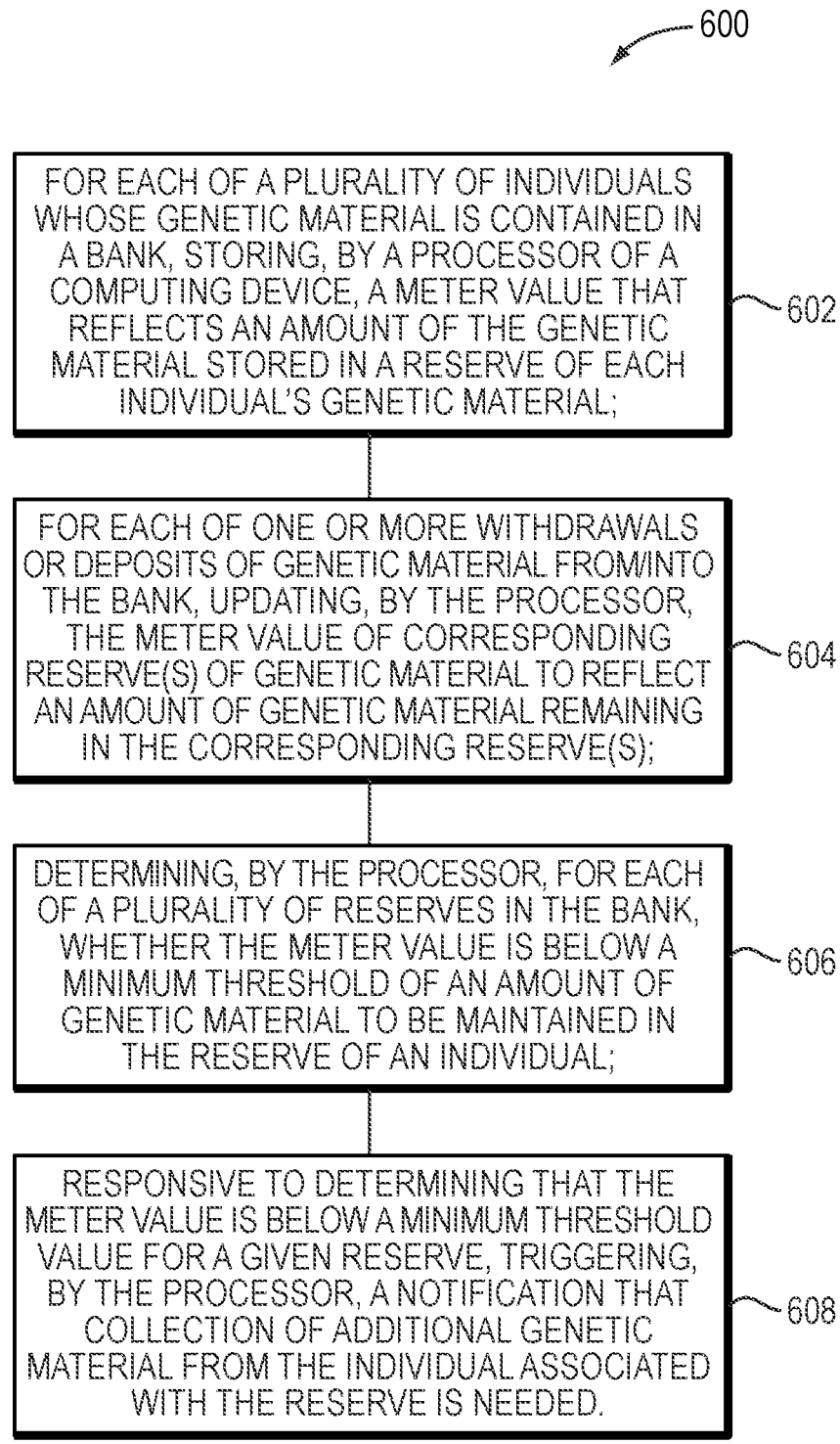
FIG. 6 is a block diagram showing a process for automated monitoring and replenishment of genetic material reserves, according to an illustrative embodiment.

Turning to FIG. 6, an example process 600 for monitoring (e.g., automatically) amounts of genetic material (e.g. DNA, e.g. RNA) stored in a reserve of genetic material extracted from biological samples of individuals (e.g. saliva, e.g. blood, e.g. tissue, e.g. cheek cells (e.g. collected via a cheek (buccal) swab, e.g. urine, e.g. hair, e.g. induced pluripotent stem cells generated from adult cells of individuals) is shown. In process 600, in one step a processor of a computing device stores a meter value for each of a plurality of individuals whose genetic material is contained in a bank (602). The meter values stored for each individual reflects an amount of genetic material stored in a reserve of the individual's genetic material. As genetic material is withdrawn and/or deposited, for example as genetic tests are run for an individual and/or genetic material is collected from the individual, the processor updates the meter value for the reserve of the individual's genetic material (604). As meter values are updated, the processor determines whether they are below a particular minimum threshold for an amount of genetic material to be maintained in the reserves (606). If a meter value for a particular reserve is determined to be below the minimum threshold, a notification is triggered to indicate that collection of additional material from the corresponding individual is needed (608).

Computer System and Network Architecture

Figure 7:
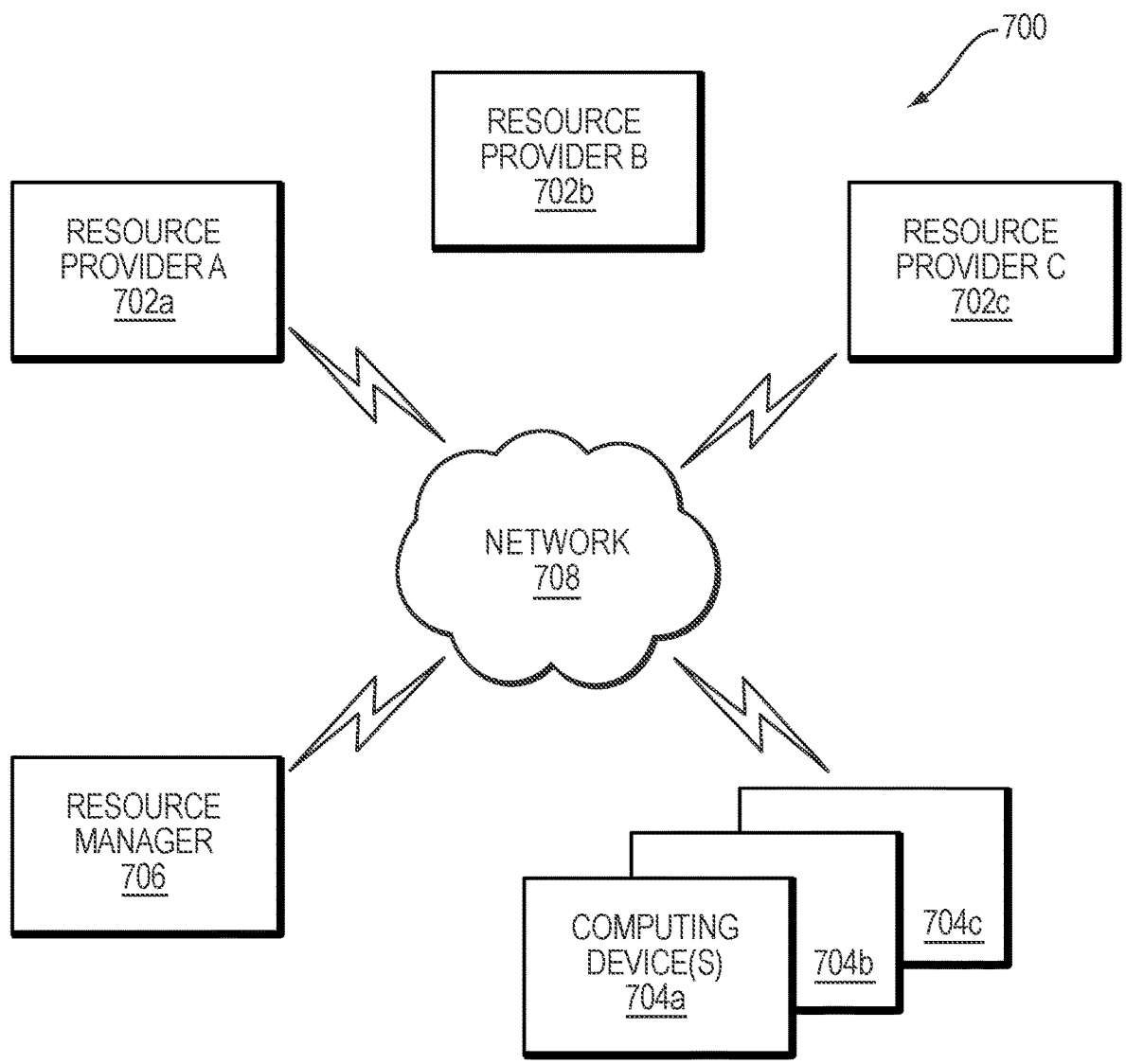
FIG. 7 is a block diagram of an exemplary cloud computing environment, used in certain embodiments.

As shown in FIG. 7, an implementation of a network environment 700 for use in providing systems, methods, and architectures described herein is shown and described. In brief overview, referring now to FIG. 7, a block diagram of an exemplary cloud computing environment 700 is shown and described. The cloud computing environment 700 may include one or more resource providers 702*a*, 702*b*, 702*c* (collectively, 702). Each resource provider 702 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 702 may be connected to any other resource provider 702 in the cloud computing environment 700. In some implementations, the resource providers 702 may be connected over a computer network 708. Each resource provider 702 may be connected to one or more computing device 704a, 704b, 704c (collectively, 704), over the computer network 708.

The cloud computing environment 700 may include a resource manager 706. The resource manager 706 may be connected to the resource providers 702 and the computing devices 704 over the computer network 708. In some implementations, the resource manager 706 may facilitate the provision of computing resources by one or more resource providers 702 to one or more computing devices 704. The resource manager 706 may receive a request for a computing resource from a particular computing device 704. The resource manager 706 may identify one or more resource providers 702 capable of providing the computing resource requested by the computing device 704. The resource manager 706 may select a resource provider 702 to provide the computing resource. The resource manager 706 may facilitate a connection between the resource provider 702 and a particular computing device 704. In some implementations, the resource manager 706 may establish a connection between a particular resource provider 702 and a particular computing device 704. In some implementations, the resource manager 706 may redirect a particular computing device 704 to a particular resource provider 702 with the requested computing resource.

Figure 8:
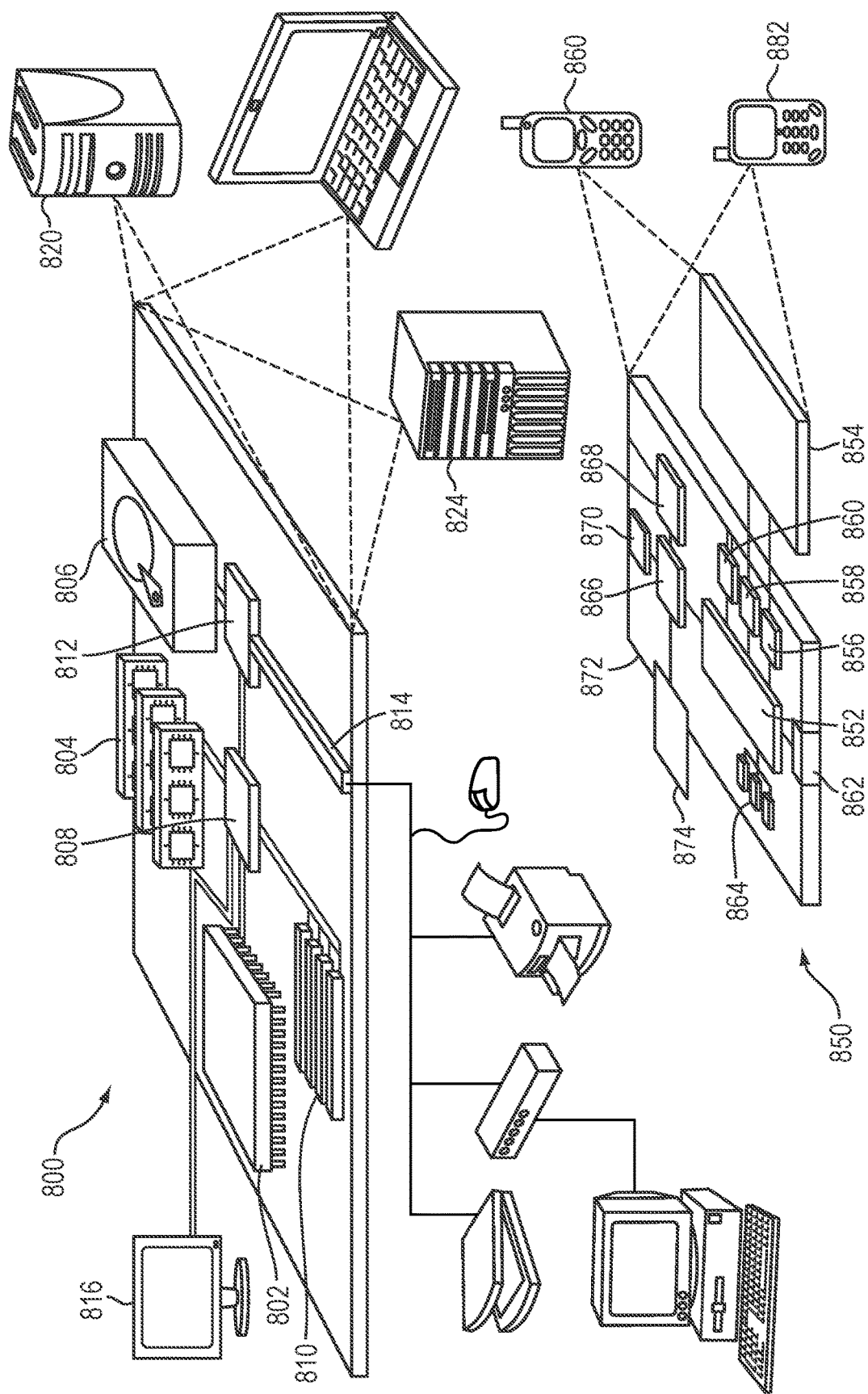
FIG. 8 is a block diagram of an example computing device and an example mobile computing device used in certain embodiments The features and advantages of the present disclosure will become more apparent from the detailed description set forth below when taken in conjunction with the drawings, in which like reference characters identify corresponding ele-

FIG. 8 shows an example of a computing device 800 and a mobile computing device 850 that can be used to implement the techniques described in this disclosure. The computing device 800 is intended to represent various forms of digital computers, such as laptops, desktops, workstations, personal digital assistants, servers, blade servers, mainframes, and other appropriate computers. The mobile computing device 850 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 800 includes a processor 802, a memory 804, a storage device 806, a high-speed interface 808 connecting to the memory 804 and multiple high-speed expansion ports 810, and a low-speed interface 812 connecting to a low-speed expansion port 814 and the storage device 806. Each of the processor 802, the memory 804, the storage device 806, the high-speed interface 808, the high-speed expansion ports 810, and the low-speed interface 812, are interconnected using various busses, and may be mounted on a common motherboard or in other manners as appropriate. The processor 802 can process instructions for execution within the computing device 800, including instructions stored in the memory 804 or on the storage device 806 to display graphical information for a GUI on an external input/output device, such as a display 816 coupled to the high-speed interface 808. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system). Thus, as the term is used herein, where a plurality of functions are described as being performed by "a processor", this encompasses embodiments wherein the plurality of functions are performed by any number of processors (one or more) of any number of computing devices (one or more). Furthermore, where a function is described as being performed by "a processor", this encompasses embodiments wherein the function is performed by any number of processors (one or more) of any number of computing devices (one or more) (e.g., in a distributed computing system).

The memory 804 stores information within the computing device 800. In some implementations, the memory 804 is a volatile memory unit or units. In some implementations, the memory 804 is a non-volatile memory unit or units. The memory 804 may also be another form of computer-readable medium, such as a magnetic or optical disk.

The storage device 806 is capable of providing mass storage for the computing device 800. In some implementations, the storage device 806 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 802), perform one or more methods, such as those described above. The instructions can also be stored by one or more storage devices such as computer- or machine-readable mediums (for example, the memory 804, the storage device 806, or memory on the processor 802).

The high-speed interface 808 manages bandwidth-intensive operations for the computing device 800, while the low-speed interface 812 manages lower bandwidth-intensive operations. Such allocation of functions is an example only. In some implementations, the high-speed interface 808 is coupled to the memory 804, the display 816 (e.g., through a graphics processor or accelerator), and to the high-speed expansion ports 810, which may accept various expansion cards (not shown). In the implementation, the low-speed interface 812 is coupled to the storage device 806 and the low-speed expansion port 814. The low-speed expansion port 814, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 800 may be implemented in a number of different forms, as shown in the figure. For example, it may be implemented as a standard server 820, or multiple times in a group of such servers. In addition, it may be implemented in a personal computer such as a laptop computer 822. It may also be implemented as part of a rack server system 824. Alternatively, components from the computing device 800 may be combined with other components in a mobile device (not shown), such as a mobile computing device 850. Each of such devices may contain one or more of the computing device 800 and the mobile computing device 850, and an entire system may be made up of multiple computing devices communicating with each other.

The mobile computing device 850 includes a processor 852, a memory 864, an input/output device such as a display 854, a communication interface 866, and a transceiver 868, among other components. The mobile computing device 850 may also be provided with a storage device, such as a micro-drive or other device, to provide additional storage. Each of the processor 852, the memory 864, the display 854, the communication interface 866, and the transceiver 868, are interconnected using various buses, and several of the components may be mounted on a common motherboard or in other manners as appropriate.

The processor 852 can execute instructions within the mobile computing device 850, including instructions stored in the memory 864. The processor 852 may be implemented as a chipset of chips that include separate and multiple analog and digital processors. The processor 852 may provide, for example, for coordination of the other components of the mobile computing device 850, such as control of user interfaces, applications run by the mobile computing device 850, and wireless communication by the mobile computing device 850.

The processor 852 may communicate with a user through a control interface 858 and a display interface 856 coupled to the display 854. The display 854 may be, for example, a TFT (Thin-Film-Transistor Liquid Crystal Display) display or an OLED (Organic Light Emitting Diode) display, or other appropriate display technology. The display interface 856 may comprise appropriate circuitry for driving the display 854 to present graphical and other information to a user. The control interface 858 may receive commands from a user and convert them for submission to the processor 852. In addition, an external interface 862 may provide communication with the processor 852, so as to enable near area communication of the mobile computing device 850 with other devices. The external interface 862 may provide, for example, for wired communication in some implementations, or for wireless communication in other implementations, and multiple interfaces may also be used.

The memory 864 stores information within the mobile computing device 850. The memory 864 can be implemented as one or more of a computer-readable medium or media, a volatile memory unit or units, or a non-volatile memory unit or units. An expansion memory 874 may also be provided and connected to the mobile computing device 850 through an expansion interface 872, which may include, for example, a SIMM (Single In Line Memory Module) card interface. The expansion memory 874 may provide extra storage space for the mobile computing device 850, or may also store applications or other information for the mobile computing device 850. Specifically, the expansion memory 874 may include instructions to carry out or supplement the processes described above, and may include secure information also. Thus, for example, the expansion memory 874 may be provide as a security module for the mobile computing device 850, and may be programmed with instructions that permit secure use of the mobile computing device 850. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier, that the instructions, when executed by one or more processing devices (for example, processor 852), perform one or more methods, such as those described above. The instructions can also be stored by one or more storage devices, such as one or more computer- or machine-readable mediums (for example, the memory 864, the expansion memory 874, or memory on the processor 852). In some implementations, the instructions can be received in a propagated signal, for example, over the transceiver 868 or the external interface 862.

The mobile computing device 850 may communicate wirelessly through the communication interface 866, which may include digital signal processing circuitry where necessary. The communication interface 866 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 868 using a radio-frequency. In addition, short-range communication may occur, such as using a Bluetooth®, Wi-Fi™, or other such transceiver (not shown). In addition, a GPS (Global Positioning System) receiver module 870 may provide additional navigation- and location-related wireless data to the mobile computing device 850, which may be used as appropriate by applications running on the mobile computing device 850.

The mobile computing device 850 may also communicate audibly using an audio codec 860, which may receive spoken information from a user and convert it to usable digital information. The audio codec 860 may likewise generate audible sound for a user, such as through a speaker, e.g., in a handset of the mobile computing device 850. Such sound may include sound from voice telephone calls, may include recorded sound (e.g., voice messages, music files, etc.) and may also include sound generated by applications operating on the mobile computing device 850.

The mobile computing device 850 may be implemented in a number of different forms, as shown in the figure. For example, it may be implemented as a cellular telephone 880. It may also be implemented as part of a smart-phone 882, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In some implementations, modules described herein can be separated, combined or incorporated into single or combined modules. Any modules depicted in the figures are not intended to limit the systems described herein to the software architectures shown therein.

It is contemplated that systems, architectures, devices, methods, and processes of the claimed invention encompass variations and adaptations developed using information from the embodiments described herein. Adaptation and/or modification of the systems, architectures, devices, methods, and processes described herein may be performed, as contemplated by this description.

Throughout the description, where articles, devices, systems, and architectures are described as having, including, or comprising specific components, or where processes and methods are described as having, including, or comprising specific steps, it is contemplated that, additionally, there are articles, devices, systems, and architectures of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

Documents are incorporated herein by reference as noted. Where there is any discrepancy in the meaning of a particular term, the meaning provided in the Definition section above is controlling.

What is claimed is:

1. A method of monitoring amounts of genetic material stored in a reserve of genetic material extracted from biological samples of individuals, the method comprising:
   for each of a plurality of individuals whose genetic material is contained in a bank, storing, by a processor of a computing device, a meter value that reflects an amount of the genetic material stored in a reserve of each individual's genetic material;
   for each of one or more withdrawals or deposits of genetic material from/into the bank, updating, by the processor, the meter value of corresponding reserve(s) of genetic material to reflect an amount of genetic material remaining in the corresponding reserve(s); and
   determining, by the processor, for each of a plurality of reserves in the bank, whether the meter value is below a minimum threshold of an amount of genetic material to be maintained in the reserve of an individual.

2. The method of claim 1, further comprising:
   responsive to determining that the meter value is below a minimum threshold value for a given reserve, triggering, by the processor, a notification.

3. The method of claim 2, wherein the triggering of the notification comprises issuing an alert of low reserve amount.

4. The method of claim 2, wherein triggering the notification comprises automatically issuing, by the processor, a request to supply the individual associated with the reserve with a kit for providing a replenishment biological sample.

5. The method of claim 4, wherein the kit comprises one or more instruments for collection of the replenishment biological sample from the individual associated with the reserve.

6. The method of claim 5, wherein the one or more instruments includes one or more cheek (buccal) swabs.

7. The method of claim 1, further comprising, responsive to determining that the meter value is below a minimum threshold value for a given reserve, replenishing the given reserve with additional genetic material extracted from a biological sample from the individual associated with the reserve.

8. The method of claim 7, wherein the additional genetic material is extracted from induced pluripotent stem cells generated from adult cells from the individual associated with the reserve.

9. The method of claim 1, comprising, initially:
   for each of a plurality of individuals, receiving, by the processor, an initial value reflecting an amount of genetic material initially present in the reserve of genetic material associated with the individual; and
   storing, by the processor, the received initial value as the meter value.

10. The method of claim 9, wherein the initial value is based on an amount of genetic material extracted from a corresponding biological sample from the individual associated with the reserve and deposited in the reserve.

11. The method of claim 1, comprising, for each of the one or more withdrawals:
    receiving, by the processor, a usage value that reflects the amount of genetic material removed in the withdrawal; and
    updating, by the processor, the meter value for the corresponding reserve using the usage value.

12. A system for monitoring amounts of genetic material stored in a reserve of genetic material extracted from biological samples of individuals, the system comprising:
   a processor; and
   a non-transitory computer readable memory having instructions stored thereon, wherein the instructions, when executed by the processor, cause the processor to:
      for each of a plurality of individuals whose genetic material is contained in a bank, store, by the processor, a meter value that reflects an amount of the genetic material stored in a reserve of each individual's genetic material;
      for each of one or more withdrawals or deposits of genetic material from/into the bank, update, by the processor, the meter value of corresponding reserve (s) of genetic material to reflect an amount of genetic material remaining in the corresponding reserve(s); and
      determine, by the processor, for each of a plurality of reserves in the bank, whether the meter value is below a minimum threshold of an amount of genetic material to be maintained in the reserve of an individual.

13. The system of claim 12, wherein the instructions, when executed by the processor, cause the processor to:
   responsive to determining that the meter value is below a minimum threshold value for a given reserve, trigger, by the processor, a notification.

14. The system of claim 13, wherein the instructions, when executed by the processor, cause the processor to:
   when triggering the notification, issue an alert of low reserve amount.

15. The system of claim 13, wherein the instructions, when executed by the processor, cause the processor to:
   when triggering the notification, automatically issue, by the processor, a request to supply the individual associated with the reserve with a kit for providing a replenishment biological sample.

16. The system of claim 15, wherein the kit comprises one or more instruments for collection of the replenishment biological sample from the individual associated with the reserve.

17. The system of claim 16, wherein the one or more instruments includes one or more cheek (buccal) swabs.

18. The system of claim 12, wherein the instructions, when executed by the processor, cause the processor to, initially:
   for each of a plurality of individuals, receive, by the processor, an initial value reflecting an amount of genetic material initially present in the reserve of genetic material associated with the individual; and
   store, by the processor, the received initial value as the meter value.

19. The system of claim 18, wherein the initial value is based on an amount of genetic material extracted from a corresponding biological sample from the individual associated with the reserve and deposited in the reserve.

20. The system of claim 12, wherein the instructions, when executed by the processor, cause the processor to, for each of the one or more withdrawals:
   receive, by the processor, a usage value that reflects the amount of genetic material removed in the withdrawal; and
   update, by the processor, the meter value for the corresponding reserve using the usage value.

* * * * *